US010521766B2

(12) United States Patent
Alvarez et al.

(10) Patent No.: US 10,521,766 B2
(45) Date of Patent: Dec. 31, 2019

(54) WINE INVENTORY MANAGEMENT SYSTEM AND METHODS

(71) Applicant: UNCORKED STUDIOS INCORPORATED, Portland, OR (US)

(72) Inventors: Marcelino Alvarez, Portland, OR (US); David Evans, Portland, OR (US); David Ewald, Portland, OR (US); John Furukawa, Portland, OR (US); Joshua D'Errico, Portland, OR (US); Joel Morrissette, Portland, OR (US); Melissa Chan, Portland, OR (US); Lee Lerner, Portland, OR (US); Miguel Higgins Moy, Portland, OR (US)

(73) Assignee: Uncorked Studios Incorporated, Portland, OR (US)

( * ) Notice: Subject to any disclaimer, the term of this patent is extended or adjusted under 35 U.S.C. 154(b) by 98 days.

(21) Appl. No.: 15/662,125

(22) Filed: Jul. 27, 2017

(65) Prior Publication Data

US 2018/0032948 A1 Feb. 1, 2018

Related U.S. Application Data

(60) Provisional application No. 62/367,604, filed on Jul. 27, 2016.

(51) Int. Cl.
*G06Q 10/08* (2012.01)
*G16H 50/20* (2018.01)
(Continued)

(52) U.S. Cl.
CPC .......... *G06Q 10/087* (2013.01); *G06Q 10/08* (2013.01); *G06Q 10/083* (2013.01);
(Continued)

(58) Field of Classification Search
CPC .... G06Q 20/203; G06Q 10/087; G06Q 10/08; G06Q 10/0875; G06Q 10/083
(Continued)

(56) References Cited

U.S. PATENT DOCUMENTS 6,536,306 B1  3/2003  Harris
2006/0026971 A1  2/2006  Sharpe
(Continued)

OTHER PUBLICATIONS

Esterl, Mike. Gatorade Taps Into Tech-Thirsty Consumers. Wall Street Journal, Eastern edition; New York, N.Y. [New York, N.Y]Mar. 11, 2016.*

(Continued)

*Primary Examiner* — Ariel J Yu
*Assistant Examiner* — Fawaad Haider
(74) *Attorney, Agent, or Firm* — McCoy Russell LLP

(57) ABSTRACT

A wine inventory management system is provided to assist a user in selecting and locating a wine from a wine collection. In one example, a wine inventory management system may comprise a smart cap having an indicator portion and a processor in communication with the smart cap. The processor in communication with the smart cap may comprise a determining module that determines a set of criteria, a matching module that matches wines to the set of criteria to form a wine set, and an illuminating module that illuminates smart caps of the wine set. The smart caps may be illuminated with different colors, light animation patterns, and with different images in some examples.

20 Claims, 12 Drawing Sheets

(51) Int. Cl.
*G16H 40/20* (2018.01)
*G06Q 20/20* (2012.01)
*G16H 10/60* (2018.01)
*G06Q 50/22* (2018.01)

(52) U.S. Cl.
CPC ....... *G06Q 10/0875* (2013.01); *G06Q 20/203* (2013.01); *G06Q 50/22* (2013.01); *G16H 10/60* (2018.01); *G16H 40/20* (2018.01); *G16H 50/20* (2018.01)

(58) Field of Classification Search
USPC .......................................................... 705/28
See application file for complete search history.

(56) References Cited

U.S. PATENT DOCUMENTS

| | | |
|---|---|---|
| 2014/0144935 A1 | 5/2014 | O'Keefe, Jr. et al. |
| 2015/0205801 A1 | 7/2015 | Tompkins |
| 2015/0278928 A1 | 10/2015 | Nichols et al. |
| 2016/0178455 A1 | 6/2016 | Astorino |

OTHER PUBLICATIONS

ISA Korean Intellectual Property Office, International Search Report and Written Opinion Issued in Application No. PCT/US2017/044242, dated Sep. 18, 2017, WIPO, 13 pages.

* cited by examiner

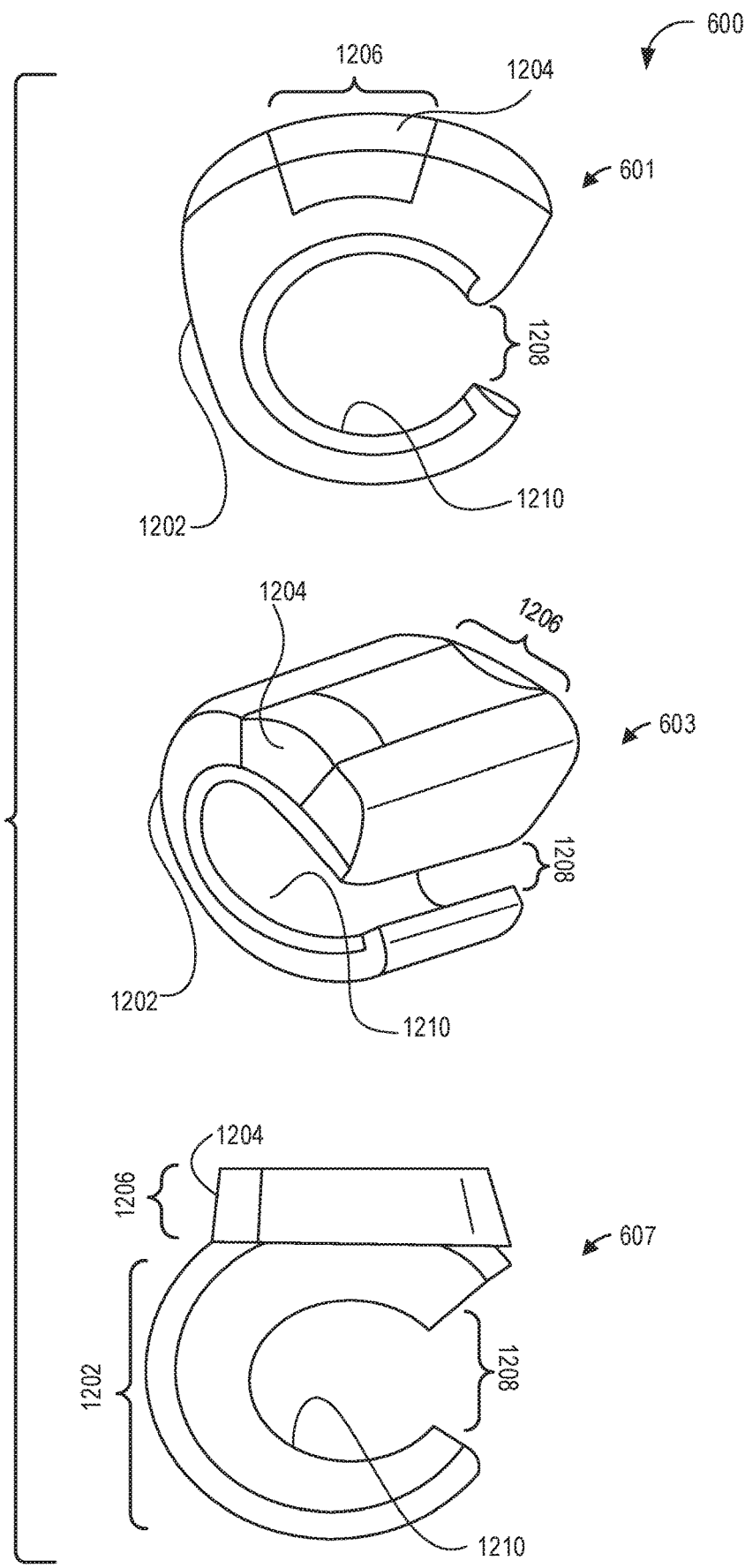

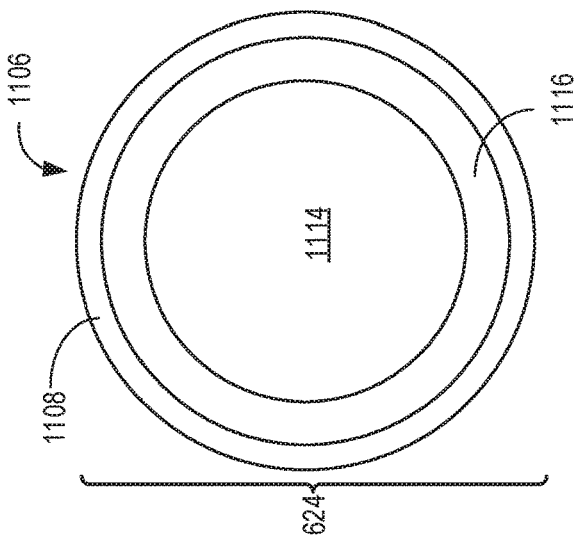
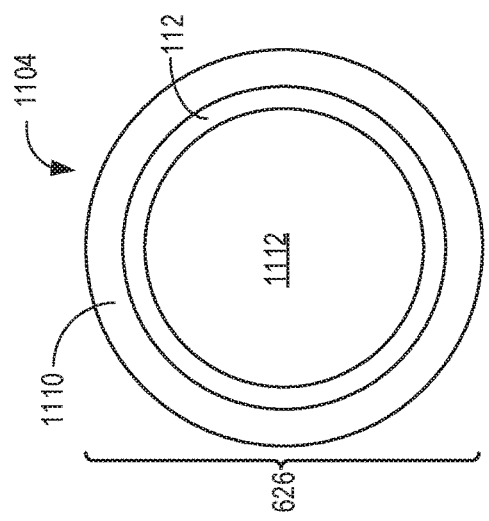
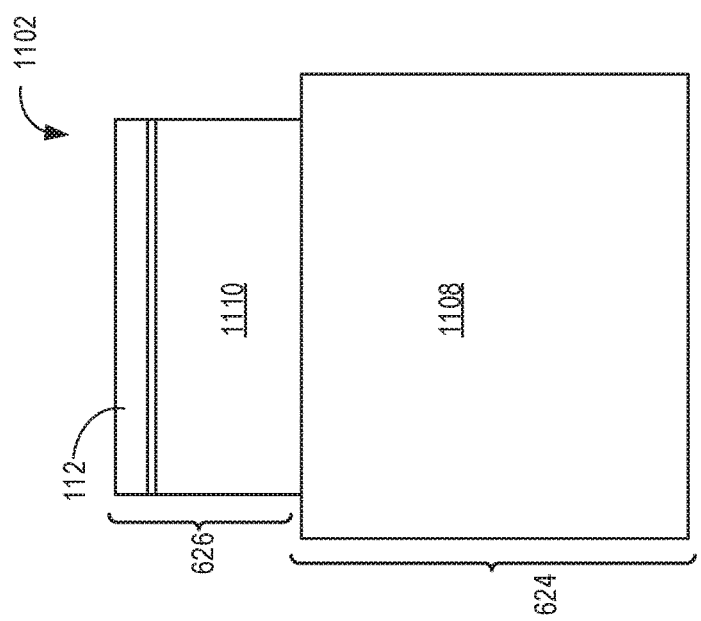
FIG. 11C
FIG. 11B
FIG. 11A

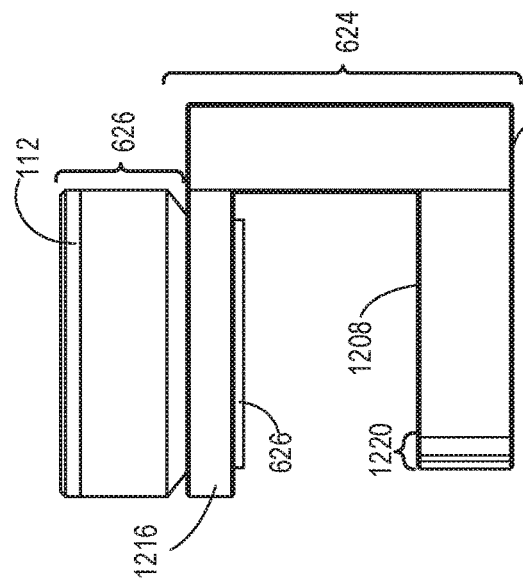
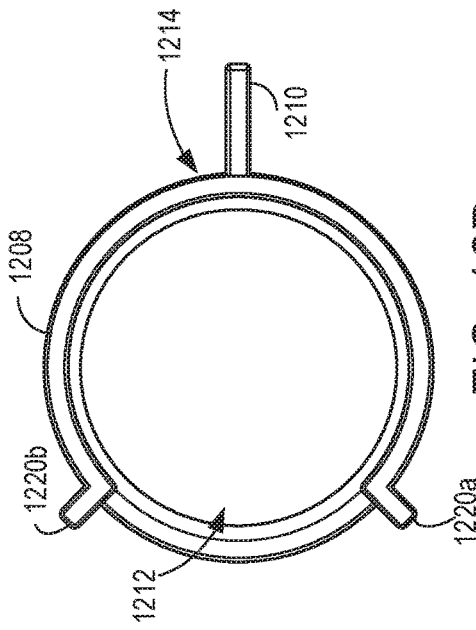
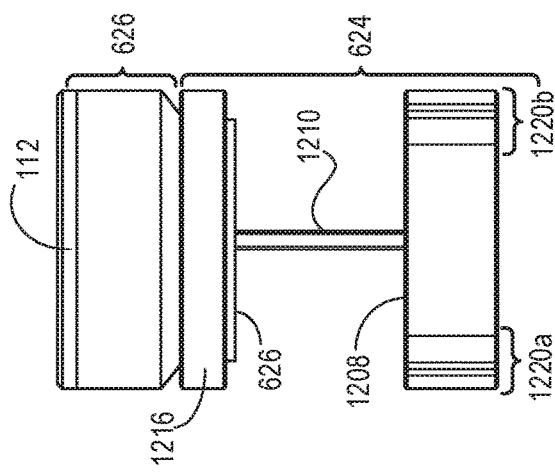
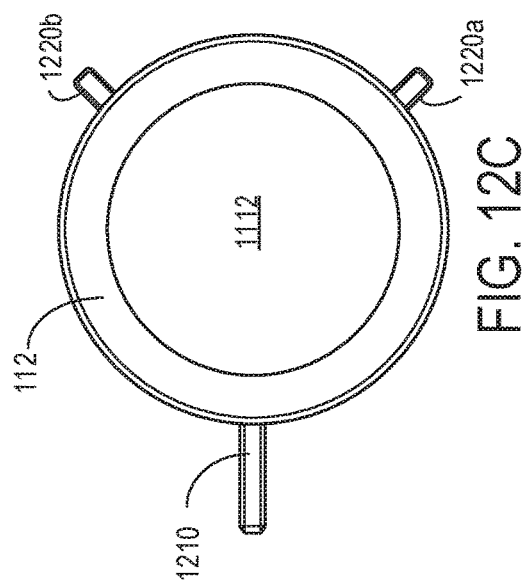
FIG. 12A
FIG. 12B
FIG. 12C
FIG. 12D

WINE INVENTORY MANAGEMENT SYSTEM AND METHODS

CROSS REFERENCE TO RELATED APPLICATIONS

The present application claims priority to U.S. Provisional Application No. 62/367,604, entitled "WINE INVENTORY MANAGEMENT SYSTEM," filed on Jul. 27, 2016, the entire contents of which are hereby incorporated by reference for all purposes.

BACKGROUND/SUMMARY

Selecting a wine from a wine collection is a decision that may take into account many variables. For example, for a wine enthusiast, there is no more vexing a question than— what wine should I drink tonight? It is a question that is filled with the promise of opportunity. After all, a great bottle of wine paired with a great meal is one of the greatest pleasures in life. But whether you are having a simple weeknight dinner or a 6 course meal, the question is not a simple one. It may require aligning technical information about wines in a current wine collection (e.g., varietal, vintage, drinkability, or cost), with emotional knowledge about the wines in the current wine collection (e.g., a special significance of the wine), and matching those insights to the meal or event for which the wine is being selected. Further, one needs to be able to find the selected wine quickly and efficiently.

Traditional inventory systems for tracking information and the locations of the wines in a wine collection often utilize spreadsheets, sticky notes, or tags that hang around the neck of each wine bottle to track information about the wines in a collection. However, these inventory systems have several drawbacks. For example, traditional inventory systems require a lot of individual attention, as the information for the wines in the wine collection is manually entered and removed. The requirement of manual entry in traditional inventory systems may result in less information about the wines being tracked due to extra effort on the part of the wine collection manager to locate, enter, and organize information about the wines in the wine collection. Further, because traditional inventory systems do not automatically update, the inventory of bottles available in a collection easily becomes inaccurate if, for example, a wine bottle is opened without it being recorded or if a wine bottle is added to the collection without it being recorded. Additionally, locating a wine in a wine collection may be inefficient using traditional inventory systems, as locating the desired wine may require reading wine bottle labels, tags, or notes.

To at least partially address these issues, a wine inventory management system and methods are provided. An example wine inventory management system may comprise hosted services communicatively coupled to an application and smart caps.

An example method for wine inventory management may comprise, responsive to a user input, comparing information about one or more wines in a wine collection to a set of criteria, determining that at least one of the of wines satisfies the set of criteria, and illuminating indicator lights of smart caps (also referred to as caps herein) that correspond with the at least one wine satisfying the set of criteria. The smart caps may be mounted on wine bottles in the wine collection. In some examples, the smart caps may be mounted over a cork or cap of a wine bottle. In other examples, the smart caps may be mounted to a neck of a wine bottle. Multiple smart caps may form a cap display. However, in some examples, a cap display may only comprise one smart cap. By illuminating indicator lights of the smart caps in a cap display that corresponds with the set of criteria, wines that meet the set of criteria may be quickly and efficiently located from a wine collection.

Further, a color of the indicator lights or other light animation, such as a light image or pulsing, that may illuminate the smart caps may correspond with a specific meaning. For example, if a wine is recommended to drink, the indicator light of the smart cap associated with the recommended wine may be illuminated in a particular color to indicate that the wine is recommended to drink. On the other hand, in an example where a wine is not recommended to drink, such as a wine that is too young, the indicator light of a smart cap may be illuminated with a different color indicating that the wine is not recommended to drink.

An example wine inventory management system comprises at least one smart cap, where each of the at least one smart cap includes one or more indicator lights, a wireless subsystem, and a microcontroller with instructions stored in non-transitory memory for illuminating the indicator lights. Each of the at least one smart cap may be mounted to a wine bottle. In some examples, the at least one smart cap may be mounted over a cork of a wine bottle. In other examples, the at least one smart cap may be mounted to a neck of the wine bottle. Each of the at least one caps may also include a plurality of sensors.

The smart caps may be illuminated in response to the smart caps receiving a request via the wireless subsystem. The smart caps may be illuminated by illuminating indicator lights of the smart caps. A smart cap may receive a request to illuminate the indicator lights responsive to a wine with which a smart cap is associated satisfying a set of criteria. In other examples, a smart cap may receive a request to illuminate its indicator lights responsive to a button of the smart cap receiving a user input. In some examples, the user input may be pressing the button of the smart cap.

The wireless subsystem of each of the smart caps may enable the formation of wireless communication links. The wireless subsystems of the smart caps may form wireless communication links with a hub system, for example. In some embodiments, the wireless subsystem may form a wireless communication link with one or more of a server (e.g., a cloud-based server) and a wine inventory device operating a wine inventory application of the wine inventory management system via the hub system. The server may support hosted services of the wine inventory management system, in some examples. In this way, the smart caps may provide an Internet of Things (IoT) based approach to at least partly address issues with traditional wine inventory systems.

BRIEF DESCRIPTION OF THE FIGURES

FIG. 6 shows various example smart caps with a C-shaped clip according to at least one embodiment of the present disclosure.

FIGS. 11A-11C show various views of another example smart cap according to at least one embodiment of the present disclosure.

FIGS. 12A-12D show various views another example smart cap according to at least one embodiment of the present disclosure.

FIGS. 3A-3C, 5A-5C, 6, and 11A-12D are drawn approximately to scale.

DETAILED DESCRIPTION

Figure 1B:
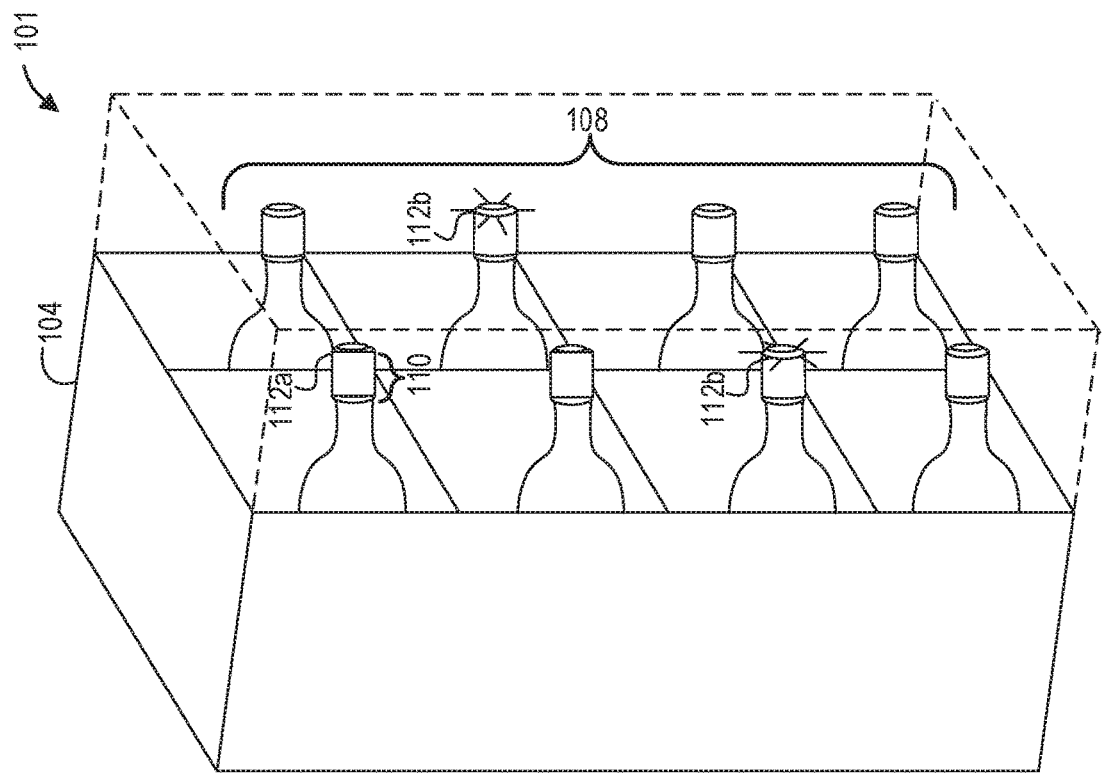
FIG. 1B shows a second view of an example wine inventory management system environment.

An example wine inventory management system is described herein. The wine inventory management system may be used in several environments. For example, the wine inventory management system may be used for a wine collection as described at FIGS. 1A-1B. The wine inventory management system may include several components that all communicate with each other as described in FIG. 2. Such components may include a hub and smart caps, which are described at FIGS. 3A-3C, 5A-5C, 6, and 1A-12D, and these components of the wine inventory management system may be set up as described at FIG. 10, for example. Reference to smart caps (also referred to as caps herein) may refer to caps including a computing system, such as the computing system described at FIG. 7. Additional components of the wine inventory management system may include a wine inventory device as described at FIG. 4 that operates a wine inventory application of the wine inventory management system and hosted services of the wine inventory management system, where details in regards to the hosted services are described herein at FIG. 8. There may be several functions achieved via the wine inventory management system. For example, components of the wine inventory management system may be paired, may provide diagnostic tests, and may convey information about wines in a wine collection. Additional functions that may be achieved by the wine inventory management system may include adding new wines to the wine inventory management system and searching for wines. These functions of the wine inventory management system may enable efficient selection of wines of a wine collection by illuminating lights of the smart caps in some examples, as described at FIG. 9.

FIGS. 3A-3C, 5A-5C, 6, and 11A-12D show the relative positioning of various components of the receiver assembly. If shown directly contacting each other, or directly coupled, then such components may be referred to as directly contacting or directly coupled, respectively, at least in one example. Similarly, components shown contiguous or adjacent to one another may be contiguous or adjacent to each other, respectively, at least in one example. As an example, components lying in face-sharing contact with each other may be referred to as in face-sharing contact or physically contacting one another.

As another example, elements positioned apart from each other with only a space there-between and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example.

As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

For purpose of discussion, FIGS. 1A-12D will be described collectively.

Figure 1A:
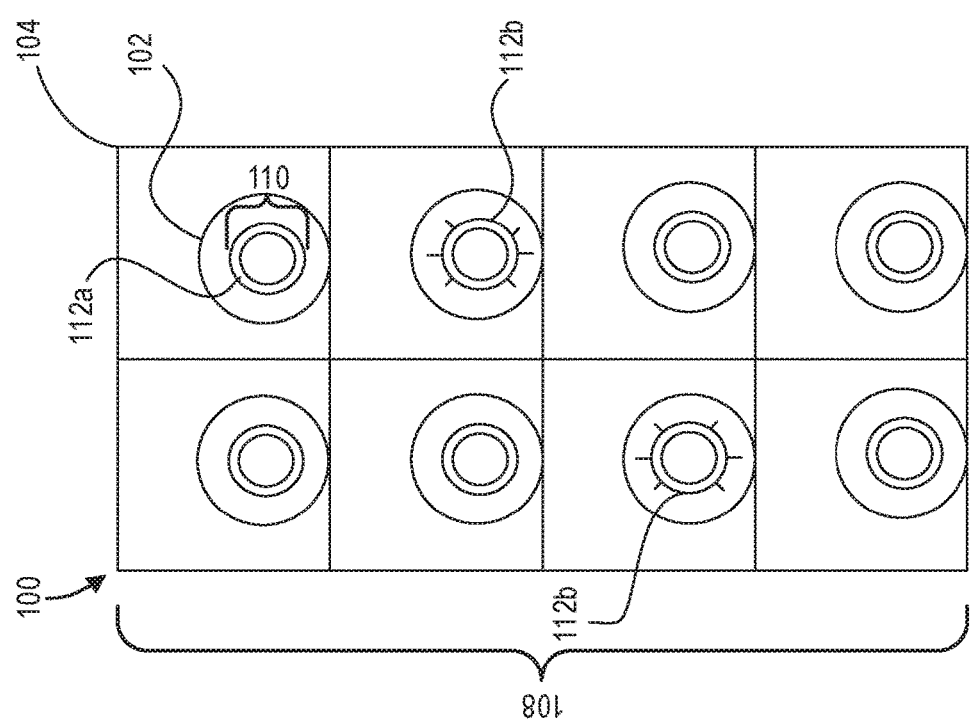
FIG. 1A shows a first view of an example wine inventory management system environment.

FIG. 1A shows a first view of an example environment 100 for a cap display 108 of a wine inventory management system, and FIG. 1B shows a second view of the example environment 101 of the cap display 108. Cap display 108 may include a plurality of smart caps 110 that may each be mounted to wine bottles 102. In some examples, the wine bottles 102 may be a part of a wine collection. Wine bottles 102 may be stored in a wine rack 104. In some examples, at least some of the wine bottles stored in a wine rack 104 may not be visible from certain angles. For example, as shown in FIG. 1B, some of the wine bottles may not be visible in cases where the wine rack 104 is as deep as indicated by the dashed lines in FIG. 1B. Thus, in examples where a wine rack may cause the wine bottles to not be visible at certain angles, the illumination of the smart caps indicator lights may be particularly advantageous to enable the location of wines in a wine collection.

In addition to the above described environment, in some embodiments, the wine bottles of a wine collection may be stored in multiple locations. For example, a wine collection may include wine bottles 102 stored in multiple buildings or different rooms. In other examples, wine bottles 102 of a wine collection may be located in a single location. For example, a wine bottle 102 of a wine collection may be stored a single room.

Cap display 108 may include smart caps 110 mounted to wine bottles 102. In some embodiments each wine bottle 102 in a wine collection may have a smart cap 110 mounted therein. In other examples, only a portion of the wine bottles 102 in a wine collection may have a smart cap 110 mounted therein. Smart caps 110 may be mounted over a cap portion of wine bottles 102. In other examples, however, smart caps 110 may be mounted to a neck of a wine bottle 102. Smart caps 110 may be mounted to wine containers aside from wine bottles 102, in some examples.

Smart caps 110 may include an indicator portion comprising a plurality of indicator lights 112 viewable from an exterior surface of the smart cap, where the indicator lights 112 may be unilluminated lights 112a or illuminated lights 112b. These indicator lights 112 may be arranged in a ring on a smart cap 110. However, other arrangements of indicator lights 112 may be possible. For example, a plurality of indicator lights 112 of a smart cap 110 may be in a linear arrangement on smart cap 110. In some examples, a plurality of lights 112 of a smart cap 110 may be arranged with a first portion of the plurality of lights 112 on a first surface of smart cap 110 and a second portion of the plurality of lights 112 on a second surface on smart cap 110. In other examples, the plurality of indicator lights 112 may be arranged with all of the indicator lights 112 on a single surface of a smart cap 110. In some embodiments, there may only be one indicator light on a smart 110, as opposed to a plurality of indicator lights. Smart caps 110 may communicate with a wine inventory device that receives input from a user (e.g., a mobile device, tablet, smart phone, etc.).

The indicator lights 112 in smart caps 110 may be illuminated to enable efficient location of a wine bottle 102. In some examples, indicator lights 112 of smart caps 110 may be illuminated responsive to smart cap 110 being associated with wines satisfying a set of criteria, the set of criteria determined responsive to a user input. In other examples, indicator lights 112 of smart caps 110 may be illuminated responsive to the smart caps themselves directly receiving a user input.

Multiple smart caps 110 may form a cap display 108. However, a cap display may only comprise one smart cap 110 in some examples. A cap display 108 may be used to efficiently communicate information about a wine collection. For example, cap display 108 may efficiently communicate the location of wines in a wine collection that satisfy a set of criteria by illuminating smart caps 110 associated with wines satisfying the set of criteria.

The indicator lights 112 may not be illuminated in a default state in order to conserve battery of smart caps 110, for example. In another example, the indicator lights 112 of the smart caps 110 may not be illuminated because none of the wines 102 associated with the smart caps 110 in cap display 108 satisfy a set of criteria for a request to illuminate these smart caps. Moreover, in at least one example, all of the caps 110 of a cap display 108 may be powered off responsive to a user input to the wine inventory management system in order to conserve power of the smart caps 110. In other examples, the wine inventory management system may have a power conservation mode where all of the smart caps 110 are intermittently powered off to conserve battery power. It is noted that powering off of the smart caps 110 may include powering off all sensors, indicator lights, etc. of the smart caps 110. Further, in at least one example, the smart caps 110 may be powered via manual input to the smart cap. In at least one example, responsive to determining that a smart cap has both been turned off and removed, the smart cap 110 may trigger a wine bottle's automatic removal from an inventory of the wine inventory management system via the wine inventory application and the wine inventory hosted services.

The example wine inventory management system may be used for various types of wine collections. For example, the wine inventory management system may be used for public, private, and shared collections. Examples of private wine collections may include private home collections, private wine lockers, private restaurant cellars, private winery storage, or wine retail stores' back-of-house inventory. Examples of public wine collections may include public restaurant cellars, public restaurant wine racks, public wine bar cellars, a public rack at a wine bar, public storage at a winery, wine trade shows, or wine retail stores' front-of-house inventory. Examples of shared wine collections may include a shared collection across multiple residences, or a wine collection that has shared remote access to wine inventory.

In addition to these different private, public, and shared types of wine collections, there may also be several additional different use environments for these types of wine collections. For example, private home collections may include private home collections stored in a single location within a single residence, stored in multiple locations within a single residence, or stored across multiple residences.

Figure 2:
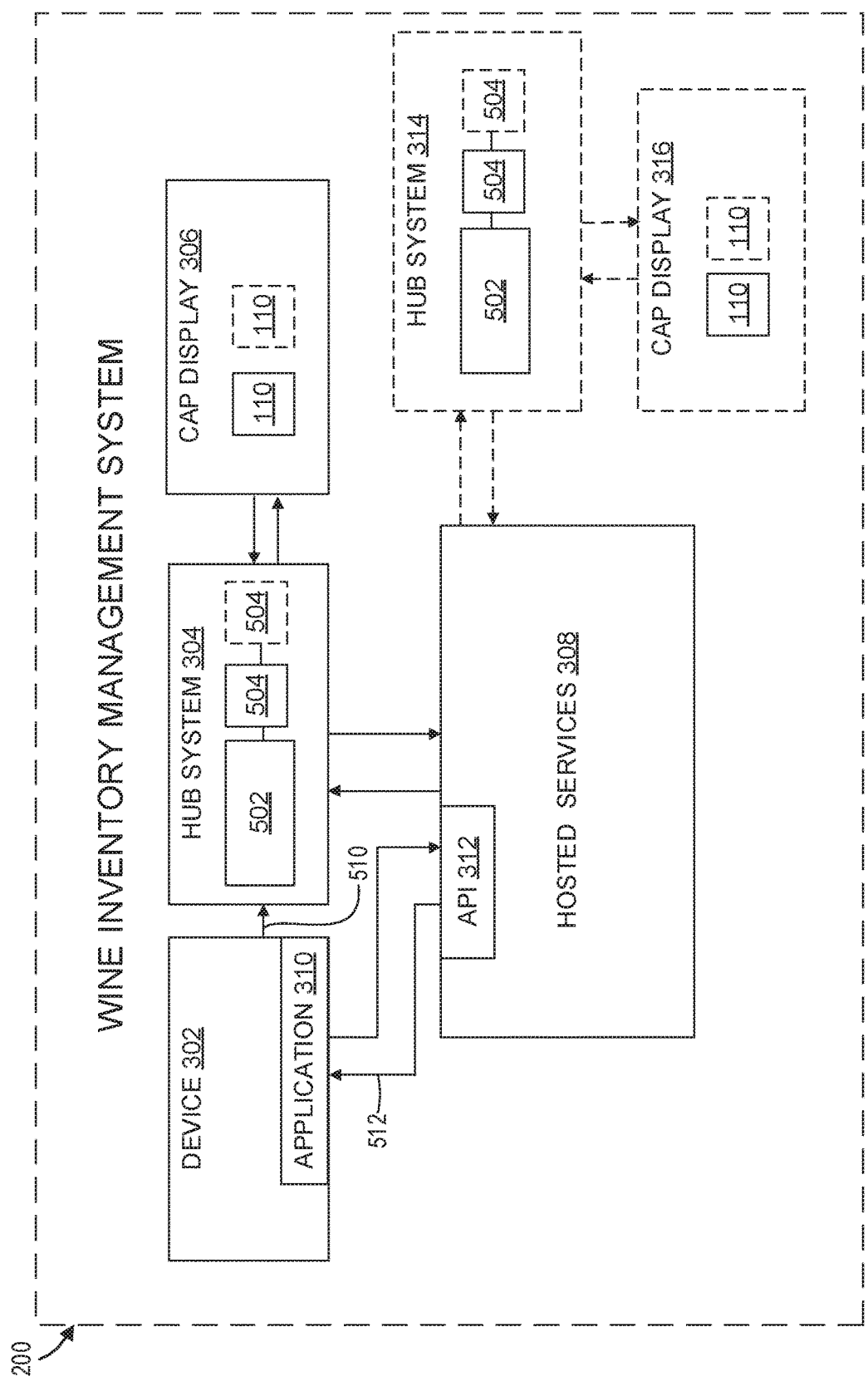
FIG. 2 shows a schematic representation of a communication flow for an example wine inventory management system according to at least one embodiment of the present disclosure.

Turning to FIG. 2, FIG. 2 shows a block diagram of an example wine inventory management system 200. The example wine inventory management system 200 may perform one or more of the methods described herein. Example wine inventory management system 200 comprises a wine inventory device 302 that operates a wine inventory application 310, a hub system 304, a cap display 306, and hosted services 308. Wine inventory device 302 may be a computing device in at least one example, as described in more detail at FIG. 4. In some examples, the wine inventory management system may include multiple cap displays and hub systems. Cap display 306 may comprise a plurality of smart caps 110. However, any number of smart caps 110 in a cap display may be possible. For example, cap display 306 may only comprise one smart cap 110.

Wine inventory device 302 may be a device that receives a user input. Wine inventory application 310 may be operated on wine inventory device 302. In some examples, wine inventory device 302 may be a mobile device (e.g., smart phone, tablet, laptop, etc.), and wine inventory application 310 may be a mobile application operated on the mobile device. Additionally or alternatively, wine inventory device 302 may be a virtual personal assistant.

Furthermore, in at least one example, wine inventory device 302 may be integrated with hub system 304. For example, in cases where the wine inventory device may be a virtual personal assistant, the wine inventory device 302 may be integrated into a hub of the hub system such that the hub of the hub system is also the wine inventory device, for example. The virtual personal assistant may perform all the functionalities of the wine inventory application 310, receiving user input via voice command. Such examples where a virtual personal assistant is integrated into the hub may be advantageous for reducing a number of separate components necessary to illuminate smart caps associated with wine meeting a particular set of criteria. Furthermore, the integration of a virtual personal assistant into the hub of the hub system may be beneficial to ensure that a user may utilize the wine inventory management system so long as the user is near the hub, even if the user does not have a wine inventory device 302 including the wine inventory application 310 with them.

Wine inventory application 310 may enable communication with wine inventory hosted services 308. In one example, wine inventory application 310 may cause the wine inventory device to communicate with wine inventory hosted services 308 via wireless communication such as Wi-Fi. However, any wireless communication protocol may be possible. For example, in some embodiments the wireless communication may be achieved via Bluetooth low energy (BLE) or near field communication (NFR) wireless communication protocols.

Wine inventory application 310 is a client application that provides a user interface between a user and the wine inventory management system. In some examples, wine inventory application 310 may display different dashboards for different types of users. Further, the different types of users may have different permissions within wine inventory application 310. For example, a user that is designated as a winery user may be a first type of user, and this first type of user may be provided a winery dashboard via wine inventory application 310 to enable addition of wines that may be associated with the winery which they represent. In some examples, a user that is designated as a winery user (the first type of user) may input wine details information about new wines or wines that are already stored in a wine database via a winery dashboard to be stored by hosted services. Such information that may be inputted by a winery user about wines may include a recommended timeframe for drinking a wine, tasting notes, the pH of the wine, the tannin content of the wine, varietal used, the residual sugar content of the wine, and processing techniques used for the wine, for example. The information inputted about by a user designated as a winery user may be added to a wine database.

Wine inventory application 310 may display a different dashboard for a second type of user that is designated as a wine collector. For example, a user that is designated as a wine collector may only have permissions to search for wines, retrieve wine recommendations, and add wines to a personal wine collection. In some examples, a wine collector user may not be able to add information about wines to a wine database of hosted services. However, in at least one example, a wine collector user may also have access to add information about wines to the wine database of the hosted services in an additive manner to the information already in the wine database. In such examples where a wine collector may have permission to add information about wines to the wine database, such added information may be first sent to a wine expert for approval prior to publishing the wine information inputted by the wine collector to the wine database. In other examples, a user designated as a winery user may have permissions to access all of the features of wine inventory application 310 that a wine collector user may access in addition to the winery dashboard features for inputting information about wines for storage in a wine database.

Wine inventory application 310 presents a user interface that bridges a physical wine collection to a digital wine collection for a user. For example, wine inventory application 310 may provide a user interface for a user to use a digital wine collection to manage a physical wine collection. The user interface provided by wine inventory application 310 may enable a user to more accurately and efficiently manage a wine collection inventory compared to traditional wine inventory management systems. Additionally, wine inventory application 310 may enable a user to explore a wine collection, even when the user is in a physically separate location from the wine collection. In some examples, wine inventory application 310 may enable a user to explore their wine collection through a series of parametric searches (e.g. vintage, varietal, pairings). Example features and flows for wine inventory application 310 will be discussed in more detail later.

Wine inventory application 310 may communicate with wine inventory hosted services 308. Wine inventory hosted services 308 may perform a majority of a computational workload of the wine inventory management system. In some examples, however, a computational workload of the wine inventory management system 200 may be shared with one or more other apparatuses in addition to wine inventory hosted services 308, and wine inventory hosted services 308 may not perform a majority of the computational workload. For example, the computational workload may be shared between one or more of wine inventory device 302, wine inventory hosted services 308, and smart caps 110. Wine inventory hosted services 308 may be supported via a cloud-based server and may include modules for collecting, processing, and transmitting data, as discussed in more detail at FIG. 8. Wine inventory hosted services 308 may also include modules for sending operational requests. For example, wine inventory hosted services 308 may include a module for sending an operational request for indicator lights to illuminate smart caps 110.

Cap display 306 comprises at least one smart cap 110. Smart caps 110 may be mounted on bottles of wine in a wine collection, and each of the smart caps 110 may be associated with the wine of the wine bottle upon which they are mounted. The association between the smart caps 110 and the wine of the wine bottle upon which they are mounted may be tracked via the hosted services 308. In one example, every bottle of wine in a wine collection may have a smart cap 110 mounted therein. In other examples, a portion of bottles of wine in a wine collection may each have a smart cap 110 mounted therein. A wine inventory management system may have a plurality of cap displays 306, 316. For example, a wine collection that is stored in physically separate locations (e.g., different rooms, different buildings, etc.) may have different a cap display at each location. In other examples, a wine inventory management system may only have one cap display.

Each smart cap 110 of a cap display may communicate with a hub system. In some examples, each smart cap 110 of a cap display may communicate with the same hub system. For example, each smart cap 110 of cap display 306 may communicate with hub system 304 and each smart cap 110 of cap display 316 may communicate with hub system 314. In other examples, however, smart caps 110 that may be a part of the same cap display may communicate with different hub systems.

Cap displays 306, 316 may be controlled and synchronized with wine inventory application 310 via hub systems 304, 314. For example, wine inventory application 310 may communicate with wine inventory hosted services 308, and wine inventory hosted services 308 may communicate with smart caps 110 of cap display 306 via hub system 304. In other examples, wine inventory application 310 may communicate directly with a hub system via a connection between the wine inventory device 302 on which wine inventory application 310 is operated and the hub system. It is noted that in at least one example one or both of hub systems 304, 314 described herein may further include repeaters or other ancillary hardware to extend the range and/or functionality of the hub(s) in the a cellar. For example, to enable longer distance communication without distortion, at least one repeater may be included the hub systems 304, 314.

Each smart cap 110 of the at least one cap display may function as a low-power sensor and lighting unit. Each smart cap 110 may include a microcontroller with instructions stored in memory for managing aspects of the smart cap's 110 functioning. In some examples, the microcontroller may include memory storing instructions for communicating with a hub system of an example wine inventory management system and illuminating indicator lights of smart caps 110 in accordance with the methods described in this disclosure. For example, the microcontroller may manage lighting of the smart cap 110, the wireless communication of the smart cap 110, and battery optimization of a battery in the smart cap 110, for example. The lighting of indicator lights to illuminate a smart cap 110 may be managed by the microcontroller via hardware or software based pulse width modulation (PWM), for example.

A smart cap 110 of a cap display may also include sensors in some examples. Sensors of a smart cap 110 may include environmental sensors (e.g., temperature, humidity, barometric pressure, accelerometer, and ambient light sensors). One or more of the sensors of a smart cap 110 may produce an output, and the output may be conveyed to a hub system via a wireless communication link.

Output from one or more sensors of the smart caps 110 may be conveyed from the hub system and to hosted services 308 for processing. In one example, hosted services 308 may use data based on sensor output of the smart caps 110 in algorithms for calculating wine drinkability. In other examples, hosted services 308 may convey data based on sensor output to wine inventory device 302, which may be displayed via wine inventory application 310.

Each of the at least one smart caps 110 of a cap display 306, 314 includes a wireless subsystem. This wireless subsystem may enable smart caps 110 to connect upstream to hosted services 308 and wine inventory application 310 through a corresponding hub system 304, 316. In some examples, the wireless subsystem may be a low-power, short range wireless subsystem. For example, the wireless subsystem may be a Bluetooth Low Energy (BLE) wireless subsystem. In other examples, the wireless subsystem may utilize radio technology, such as radio frequency identification (RFID). For example, MHz-range RFID may be utilized (e.g., 915 Mhz band RFID). Other MHz bands may be used in at least one example. Smart caps 110 that communicate with a hub system utilizing RFID may include RFID antennae. In still other examples, the wireless subsystem may be an acoustic or quantum based wireless subsystem. Radio technology may be advantageous for the wireless subsystems of some example wine inventory management systems, as RFID is suited for supporting a large number of devices. In some examples, BLE may not be able to support more than threshold number of devices in close proximity and may be on a more restrained power budget when active as compared to RFID.

Because wireless subsystems of smart caps 110 of a cap display 306, 316 utilize a low-power and short-range radio technology (e.g., BLE, RFID), the system may include a hub system to marshal traffic between the cap display and the hosted services.

Some example wine inventory management systems may only include one hub system. However, based on user research, a significant number of wine collectors keep their collections in several physically separate locations (e.g., physically separated rooms, buildings, etc.). As a result, the wine inventory management system disclosed herein may support one or more hub systems all logically connected via backend services (i.e., hosted services 308). The dashed lines of hub system 314 and cap display 316 in FIG. 2 indicate an example wine inventory management system that includes multiple hub systems (i.e., any number of hub systems greater than one) and their associated cap displays.

Hub systems 304, 314 may contain one or more radios 504. The hub systems may contain at least a number of radios 504 required to support the number of smart caps 110 in the cap display with which they may be associated, in some examples. In embodiments where a hub system 304, 314 utilizes RFID, the hub system may contain one or more external room level reader apparatuses, mounted separately from the hub system to maintain connectivity with an associated cap display. Moreover, as mentioned above, range extenders may be included in one more of the hub systems in order to prevent distortion or loss of a signal due to long distance communication. For example, hub system 314 may include a repeater to replicate signals to ensure that a signal is not lost during communication between the one or more radios of the hub systems.

In some examples, hub systems 304, 314 may include sensors for environmental monitoring (e.g., temperature, humidity, barometric pressure, accelerometer, and ambient light sensors). For example, data based on output from environmental sensors of the hub systems 304, 314 may transmitted to hosted services 308 for processing. In some example wine inventory management systems, both the hub system(s) 304, 314 and the smart caps 110 may include sensors for environmental monitoring.

Wine inventory management systems where both the hub systems and the smart caps include sensors for environmental monitoring may be advantageous for accurate monitoring of an environment of a wine collection by sampling more regions of an example environment.

In other examples, only smart caps 110 may include sensors for environmental monitoring. Wine inventory management systems where only smart caps 110 include sensors may be advantageous for simplifying a hub system while still monitoring the environmental conditions of multiple regions in an environment of a wine collection.

In some embodiments, only the hub systems may include sensors for environmental monitoring of a wine collection. Embodiments where only the hub systems may include sensors for environmental monitoring of a wine collection may be advantageous for reducing a number of components inside the smart cap 110, which has packaging constraints, and advantageous for conserving a battery of smart wine caps 110.

In other examples still, neither the hub systems nor the smart caps may include sensors for environmental monitoring, which may simplify construction of both the hub systems and the smart caps.

Hub systems 304, 314 may also contain one or more connections as required to support connecting upstream to hosted services 308. For example, hub systems 304, 314 may include one or more of Wi-Fi and a hardwired Ethernet connection. Hub systems 304, 314 may also run embedded firmware or an operating system as required to support the radios and upstream connection to hosted services 308. Hub systems 304, 314 may be housed in a custom enclosure, designed to complement the aesthetic of the disclosed wine inventory management system, as will be described in greater detail later. In some embodiments, hub systems 304, 314 may be operated off of a main power supply due to the power consumption requirements of the hub systems. However, the hub systems 304, 314 may be battery powered in some examples.

In some example wine inventory management systems, hub systems 304, 314 may be uniquely identifiable, so that hosted services 308 may associate each hub system 304, 314 with a physical location and cap display 306, 316. Hub systems 304, 314 may also manage an active connection to the smart caps 110 and may manage reconnection of smart caps 110 that have disconnected. For example, if a smart cap 110 becomes disconnected, the hub associated with the smart cap 110 may actively look for smart cap 110 until smart cap 110 is reconnected. In some examples, hub systems 304, 314 may also be able to hand off connections of smart caps 110 between hub systems responsive to smart caps 110 being physically relocated closer to another hub.

For example, a smart cap 110 of cap display 306 may be associated with hub system 304; however, if the smart cap 110 of cap display 306 is physically relocated to be within a threshold distance of hub system 316, then hub system 304 may hand off the connection of that smart cap 110 to hub system 316. Following a connection hand off from a first hub system to a second hub system, a smart cap 110 may then become associated with the cap display controlled by the second hub system.

In some examples, hub systems 304, 314 may also manage the transmission power and connection intervals of smart caps 110 to optimize battery life of the smart cap 110 batteries. For example, smart caps 110 that may be physically closer to their associated hub may use a lower transmission power to connect. On the other hand, smart caps 110 that may be further away from their associated hub may have their transmission power increased for connection.

The wireless subsystem of a smart cap 110 may be utilized to create a communication link with a hub system, such as hub systems 304, 314. In some examples, smart caps 110 may create communication links with a hub system responsive to the hub system being within a threshold distance. In other examples, the smart caps 110 may create communication links with a hub system responsive to a user input. In some examples, if a smart cap is paired with a first hub system and then moved to a location that greater than a threshold distance for connecting to the first hub system, that smart cap may attempt to pair with a second hub system if the second hub system is within the threshold distance for connection.

The communication links created between smart caps 110 of cap displays 306, 316 and hub systems 304, 314 may be two-way communication links. However, it is also possible that the communication links created between smart caps 110 of cap displays 306, 316 and hub systems 304, 314 may be one-way communication links. In other embodiments, it may also be possible that the communication links formed between the smart caps 110 of cap displays 306, 316 and hub systems 304, 314 may include both one-way and two-way communication links.

Wine inventory application 310, through wine inventory hosted services 308 and hub systems, may control the smart caps 110 as a coordinated cap display, lighting and changing colors of the caps in coordination with user interaction. For example, the smart caps 110 of a cap display, such as cap display 306 or 316, may be coordinated to illuminate indicator lights of the smart caps 110 in particular colors responsive to user input.

In one example, the coordinated display may include simultaneously illuminating all of the smart caps in a collection that meet a set of criteria. For example, a smart cap may be illuminated responsive to being associated with a wine that meets a set of criteria. A smart cap may be illuminated by illuminating indicator lights of the smart cap. In some examples, the set of criteria may be adjusted as search results (e.g., search results for a wine via wine inventory application 310) become more general or more specific in response to user input.

In one example, all of the smart caps 110 associated with a wine that satisfies a first set of criteria may be illuminated. Then, all of the smart caps 110 associated with a wine that satisfies a second set of criteria may be requested to be illuminated, where the second set of criteria is different than the first set of criteria. In this example, if a smart cap 110 is associated with a wine that satisfied the first set of criteria but did not satisfy the second set of criteria, then that smart cap 110 would be illuminated in response to satisfying the first set of criteria and transitioned from being illuminated to not being illuminated in response to the second set of criteria. In another example, if a smart cap 110 is associated with a wine that did not satisfy the first set of criteria but satisfied the second set of criteria, then the smart cap would not be illuminated in response to the first set of criteria and would be transitioned from not illuminated to illuminated in response to the second criteria. However, in some examples, the smart caps may not be transitioned between being illuminated and not illuminated in response to satisfying or not satisfying criteria. For example, rather than illuminating or not illuminating the indicator lights in response to wines associated with the smart caps 110 satisfying or not satisfying a set of criteria, a color of the indicator lights may instead be changed. In one embodiment, this may include illuminating the indicator lights of smart caps 110 associated with wines that satisfy a set of criteria a first color and illuminating the indicator lights of smart caps 110 associated with wines that do not satisfy the first set of criteria a second color.

In still another embodiment, the indicator lights of smart caps 110 associated with wines that meet a first set of criteria may be illuminated in a first color, and indicator lights of smart caps 110 associated with wines that meet a second set of criteria may be illuminated in a second color. For example, if a user wanted to see how many white wines and red wines there may be in a wine collection via a cap display, such as cap display 306 or 316, then all smart caps 110 that may be associated with white wines may be illuminated a first color while all of the red wines may be illuminated a second color. While there may only be a first set of criteria and a second set of criteria in this example (i.e., white wines and red wines), additional sets of criteria may be possible.

Further, in addition to or as an alternative to indicating whether or not criteria is satisfied via illuminating indicator lights of smart caps a particular color, animated lighting patterns may be used. For example, animated lighting patterns (e.g., fades, sweeps across the caps, and pulsing patterns) may be changed in response to a smart cap satisfying or not satisfying a set of criteria. Additionally, these animated lighting patterns may be used in combination with another of the above approaches for indicating whether or not a wine associated with a smart cap 110 satisfies a set of criteria.

For example, if a smart wine cap 110 is associated with a wine that has emotional information attached to it (e.g., a wine indicated by a user via wine inventory application 310 to be a special occasion wine), then that smart cap may include a particular light animation if it is illuminated. That way, if a the wine that has emotional information attached to it also satisfies a set of criteria during a user wine search, there may be an additional indication to distinguish that wine from the rest of the wine collection. In other embodiments, an animated lighting pattern may be changed from a first animated pattern to a second animated pattern in response to a wine associated with a smart cap satisfying or not satisfying a set of criteria. Additionally, animated lighting patterns on the collection may also be repeated at certain time intervals, rather than in response to smart caps 110 in a cap display 306, 316 being associated with wines that satisfy a set of criteria. For example, indicator lights on smart caps 110 of cap displays, such as displays 306, 316, may be controlled to provide animated lighting patterns (e.g., fades, sweeps across the caps of the collection, pulsing patterns, etc.) at certain time intervals.

Regarding communication flow of the wine inventory management system, as discussed above, example wine inventory management system 200 includes wine inventory device 302 which operates wine inventory application 310. Wine inventory application 310 is a client application that provides a user interface between a user and example wine inventory management system 400. Wine inventory application 310 receives user input from user via a wine inventory device 302. For example, wine inventory device 302 may receive a user input from a user via a touch screen. In other examples, wine inventory device 302 may receive a user input via voice command or a mouse. In examples where a voice command is used for a user input, the voice command may be received via microphones of wine inventory device 302. Wine inventory application 310 communicates with wine inventory hosted services 308. Wine inventory hosted services 308 communicates with wine inventory application 310 and cap display 306. Wine inventory hosted services and cap display 306 communicate via a hub system 304. In some examples, there may be multiple cap displays 306. Communication between wine inventory application 310, wine inventory hosted services 308, hub system(s) 304, 314 and cap display(s) 306, 316 may be established via communication links. These communication links may be wireless communication links, for example. In some examples, these communication links may be two-way communication links. In other embodiments, it may be possible for some of the above described communication links to be one-way communication links. The wireless communication links may be BLE, Wi-Fi, or RFID communication links for example. Communication links may also be hardwired links via Ethernet or USB connection.

Hub 502 may be a part of a hub system 304 and may include at least a number of radios 504 required to support a number of smart caps 110 in a cap display 306 with which it is associated. Communication link 510 may also be a wireless communication link. Hub 502 of hub system 304 may communicate with at least one smart cap 110 of a cap display 306 via one or more radios 504. In one embodiment, smart caps 110 of cap display 306 may communicate with hub system 304 via radio technology. The radio technology may be any one of a range of radiofrequency bands that is sufficient to enable the hub system 304 to communicate with the wine inventory hosted services, the smart caps, and the wine inventory device. In one example, smart caps 110 of cap display 306 may communicate with hub system 304 via radio frequency identification (RFID) technology. In other examples, however, smart caps 110 of cap display 306 may communicate with hub system 304 via a Bluetooth Low Energy (BLE) wireless link.

Hub 502 of hub system 304 may include one or more of Wi-Fi and a hardwired Ethernet connection. Hub 502 of hub system 304 may also run embedded firmware or an operating system as required to support the radios 504 and upstream connection to server 514.

Figure 3A:
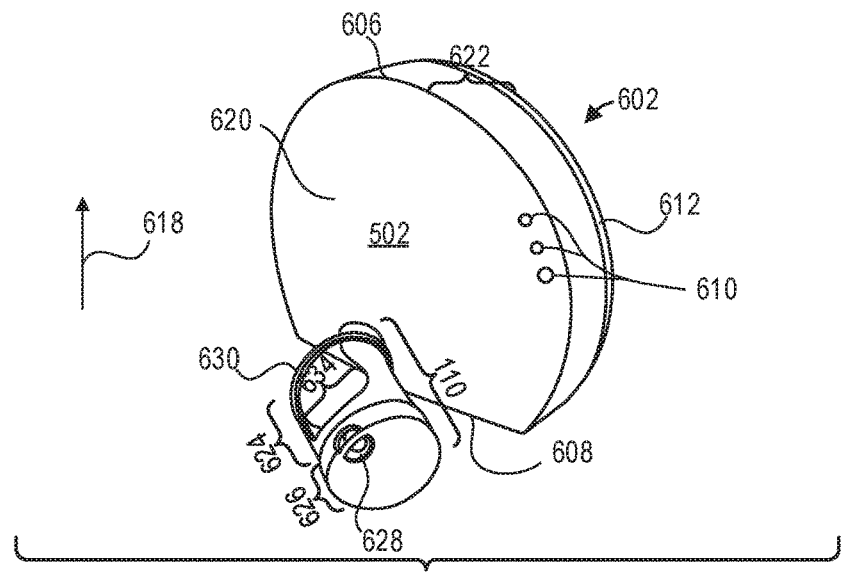
FIGS. 3A-3C show isometric views of an example hub and an example smart cap.
Figure 3B:
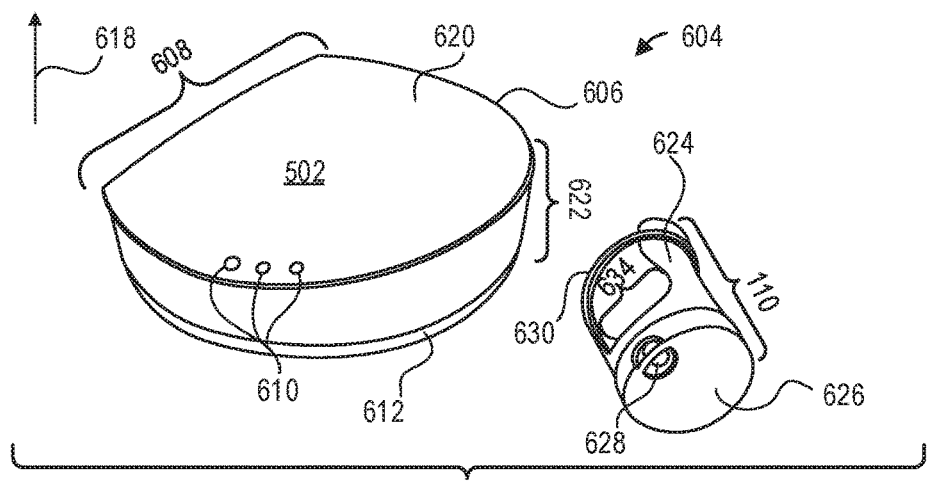
Figure 3C:
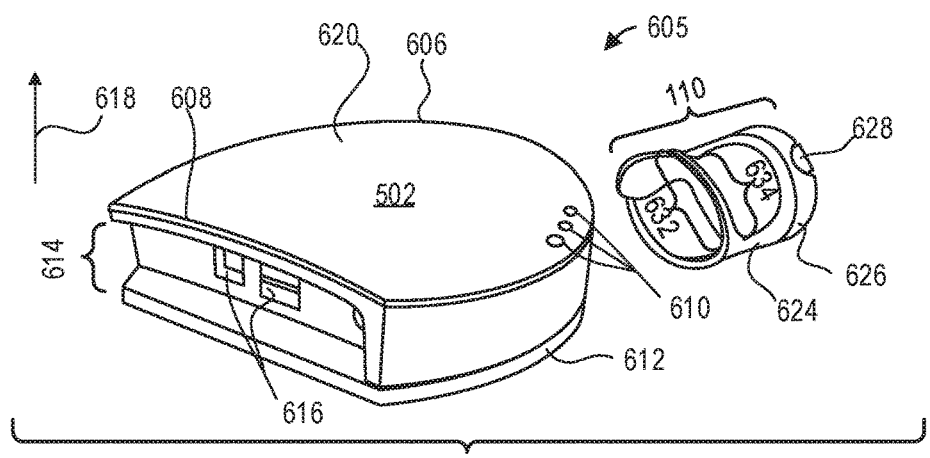

Turning now to FIGS. 3A-3C, isometric views of an example hub 502 and an example smart cap 110 are shown. The example hub 502 may be described relative to a vertical axis 618, which points opposite a direction of the force of gravity. Hub 502 may be positioned in either a base position as shown in view 604 at FIG. 3B and as shown in view 605 at FIG. 3C, or hub 502 may be positioned in a portrait position as shown in view 602 at FIG. 3A. It is noted that the view 605 of hub 502 at FIG. 3C is a back isometric view of the hub in a base position, and the view 604 of hub 502 at FIG. 3B is a front isometric view of the hub in a base position. Similarly, FIG. 3B is a shows a front isometric view of the smart cap 110 and FIG. 3C shows a back isometric view of the smart cap 110. Hub 502 may have a metalized aluminum anodized finish and may be made of a molded polycarbonate. However, other materials and finishes may be possible for hub 502. Further, other shapes and configurations of hub 502 may also be possible without departing from the scope of the invention.

Hub 502 may include a base surface 612. Base surface 612 of hub 502 may comprise an anti-slip material in some examples. This anti-slip material of base surface 612 may be a rubber, for example. Base surface 612 may be a substantially flat, planar surface. In some examples, base surface 612 may include texturing in order to improve anti-slip qualities of the surface. Base surface 612 may be a bottom surface of hub 502 when hub 502 may be in a base position, such as shown in views 604, 605. Base surface 612 may oppose an indicator surface 620 of hub 502. Indicator surface 620 of hub 502 may include a plurality of indicator lights 610. In some examples, however, indicator surface 620 of hub 502 may only include one indicator light. In other examples, indicator lights 610 of hub 502 may be located on another surface of hub 502. For example, indicator lights 610 of hub 502 may be located on a surface between indicator surface 620 and base surface 612.

Indicator surface 620 of hub 502 may be a top surface of hub 502 when in a base position, as shown in views 604, 605. Indicator surface 620 may be a curved surface. The indicator lights 610 may be illuminated to convey different statuses regarding hub 502, for example. Indicator lights 610 of hub 502 may be frosted acrylic light pipes that convey statuses about power, linking, and pairing of hub 502. For example, the pairing status may include pairing status of hub 502 with smart caps 110 of a cap display. In some examples, there may be three frosted acrylic light pipes in hub 502. However, any number of indicator lights 610 of hub 502 may be possible. Moreover, in at least one example, a ring of indicator lights may be formed around the hub 502 in addition to or alternatively to individual indicator lights 610.

Indicator light(s) 610 may be illuminated in different colors or light animation patterns to convey different statuses of hub 502. For example, indicator light(s) 610 may have a specific indicator light code 508 for the different light colors and light animation patterns that may correspond to the statuses of hub 502. Example statuses may relate to whether hub 502 is pairing with smart caps 110, an internet connection status of hub 502, and whether hub 502 is on or off.

For example, if indicator lights 610 of hub 502 are not illuminated, that may indicate that hub 502 may be turned off or unplugged. In another example, if an on/off status indicator light of hub 502 is illuminated a solid green, that may indicate that hub 502 may be turned on and working properly. If an internet connection status indicator light of hub 502 is flashing and an amber color, then that may indicate that hub 502 may not be set up or may not be able to establish an internet connection. If a link status indicator light of hub 502 is a solid amber color, then that may indicate that hub 502 may be starting up. In another example, if a link status indicator light of hub 502 is flashing amber and green, then that may indicate that hub 502 may be having a problem starting up. It is noted that while the indicator lights 610 of the hub may be arranged in a linear fashion, as shown in FIGS. 3A-3C, in at least one example the indicator lights 610 may form a ring in a top surface 620 of the hub 502. Such an arrangement to form a ring of indicator lights 610 in the top surface of the hub 502 may be beneficial to improve a visibility of the light of hub 502, for example.

Base surface 612 and indicator surface 620 may both include a curved side 606 and a portrait base side 608. Portrait base side 608 of base surface 612 and indicator surface 620 may be substantially flat. Portrait base side 608 of base surface 612 and indicator surface 620 may form a cutout 614. Cutout 614 may be an opening on an end of portrait base side 608 that may be opposite of an end where indicator lights 610 may be located. An end of portrait base side 608 that may be on the same end as where indicator lights 610 may be located may not include a cutout.

Cutout 614 may form an opening for a wire dress to feed through the cutout 614 in order to enable hub 502 to be more stable when in a portrait position. For example, at a portrait base side 608, hub 502 may include a plurality of ports 616 for accepting different wire connections. Wire connections from ports 616 may then be routed through cutout 614 of hub 502. Because wire connections may be routed through cutout 614 of hub 502, the portrait base side 608 of base surface 612 and indicator surface 620, may be the bottom of hub 502 in a portrait position, as shown in view 602 at FIG. 3A. Having portrait base side 608 of base surface 612 and indicator surface 620 being the bottom of hub 502 when hub 502 may be in a portrait position may enable hub 502 to be stable in a portrait position. Further, because an end of portrait base side 608 opposite of the end with cutout 614 does not have a cutout, wire connections to hub 502 may be hidden from view when viewing hub 502 on a side where indicator lights 506 may be located when hub 502 may be in portrait position. However, it is noted that in at least one example that the hub may be completely rounded in shape. In such examples where the hub may be completely rounded in shape, portrait base side 608 may instead be rounded instead of flat, and the hub may only rest in a base position, and the hub may not rest in a portrait position. For example, in at least one embodiment, the hub 502 may be completely rounded such that the hub is substantially circular in shape and the indicator lights 610 may be arranged in a ring that runs along the perimeter of the indicator surface 620 surface of the hub 502. Additionally or alternatively, in examples where the hub 502 may be circular in shape and include indicator lights 610 in a ring configuration, the ring may be visible on a side surface 622 of the hub 502.

Figure 4:
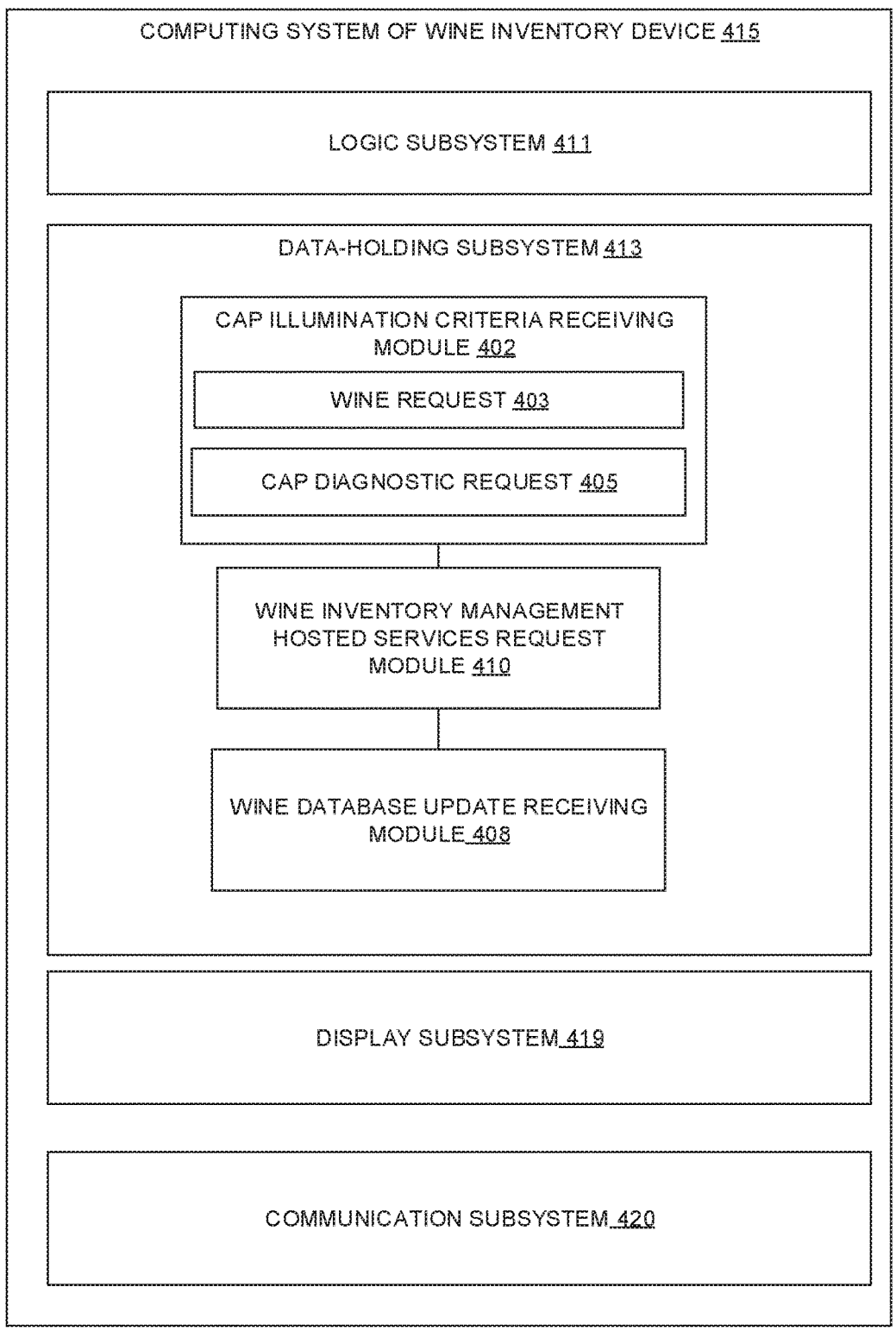
FIG. 4 shows a block diagram of an example computing system of a wine inventory device of the wine inventory management system according to at least embodiment of the present disclosure.

Turning now to FIG. 4, FIG. 4 shows an example block diagram 400 of a computing system of a wine inventory device 415 according to at least one embodiment of the present disclosure. It is noted that the computing system described in relation to FIG. 4 may be the computing system of a wine inventory device such as wine inventory device 302, for example. Additionally or alternatively, the computing system described in relation to FIG. 4 may be the computing system of the hub in examples where the hub may include a virtual assistant integrated therein.

Computing system of the wine inventory device 415 schematically shows a non-limiting computing system that may perform one or more of the methods and processes described herein. For example, the instructions stored in data-holding subsystem 413, and in some examples, in combination with the data-holding subsystems of other components of the wine inventory management system, may be instructions executable by the logic subsystem 411 to implement the herein described methods and processes disclosed at FIGS. 9-10. It is to be understood that virtually any computer architecture may be used for a computing device without departing from the scope of this disclosure. For example, the architecture shown in FIG. 4 for the data-holding subsystem 413 may differ, so that one or more of the modules 402, 403, 405, 410, and 408 may be configured for performing more or fewer tasks. In different embodiments, computing system of the wine inventory device 415 may take the form of a mainframe computer, server computer, desktop computer, laptop computer, tablet computer, home entertainment computer, network computing device, mobile computing device, mobile communication device, gaming device, etc.

Computing system of the wine inventory device 415 includes a logic subsystem 411 and a data-holding subsystem 413. Computing system of the wine inventory device 415 may optionally include other components not shown in FIG. 4. For example, computing system 415 may also optionally include user input devices such as keyboards, mice, game controllers, cameras, microphones, and/or touch screens.

Logic subsystem 411 may include one or more physical devices configured to execute one or more instructions. For example, logic subsystem 411 may be configured to execute one or more instructions that are part of one or more applications, services, programs, routines, libraries, objects, components, data structures, or other logical constructs. Such instructions may be implemented to perform a task, implement a data type, transform the state of one or more devices, or otherwise arrive at a desired result.

Logic subsystem 411 may include one or more processors that are configured to execute software instructions. Additionally or alternatively, the logic subsystem 411 may include one or more hardware or firmware logic machines configured to execute hardware or firmware instructions. Processors of the logic subsystem 411 may be single core or multi-core, and the programs executed thereon may be configured for parallel or distributed processing. The logic subsystem 411 may optionally include individual components that are distributed throughout two or more devices, which may be remotely located and/or configured for coordinated processing. One or more aspects of the logic subsystem 411 may be virtualized and executed by remotely accessible networked computing devices configured in a cloud computing configuration.

Data-holding subsystem 413 may include one or more physical, non-transitory devices configured to hold data and/or instructions executable by the logic subsystem 411 to implement the herein described methods and processes. When such methods and processes are implemented, the state of data-holding subsystem may be transformed (for example, to hold different data).

Data-holding subsystem 413 may include removable media and/or built-in devices. Data-holding subsystem 413 may include optical memory (for example, CD, DVD, HD-DVD, Blu-Ray Disc, etc.), and/or magnetic memory devices (for example, hard disk drive, floppy disk drive, tape drive, MRAM, etc.), and the like. Data-holding subsystem 413 may include devices with one or more of the following characteristics: volatile, nonvolatile, dynamic, static, read/write, read-only, random access, sequential access, location addressable, file addressable, and content addressable. In some embodiments, logic subsystem 413 and data-holding subsystem 413 may be integrated into one or more common devices, such as an application specific integrated circuit or a system on a chip.

It is to be appreciated that data-holding subsystem 413 includes one or more physical, non-transitory devices. In contrast, in some embodiments aspects of the instructions described herein may be propagated in a transitory fashion by a pure signal (for example, an electromagnetic signal, an optical signal, etc.) that is not held by a physical device for at least a finite duration. Furthermore, data and/or other forms of information pertaining to the present disclosure may be propagated by a pure signal.

When included, display subsystem 419 may be used to present a visual representation of data held by data-holding subsystem 413. For example, the display subsystem 419 may provide displays associated with wine inventory application 310 via the wine inventory device 302, where the wine inventory device 302 may be a mobile device such as a tablet or a mobile phone, for example.

As the herein described methods and processes change the data held by the data-holding subsystem 413, and thus transform the state of the data-holding subsystem 413, the state of display subsystem 419 may likewise be transformed to visually represent changes in the underlying data. Display subsystem 419 may include one or more display devices utilizing virtually any type of technology. Such display devices may be combined with logic subsystem 411 and/or data-holding subsystem 413 in a shared enclosure, or such display devices may be peripheral display devices.

It is noted that one or more of the hub 502, the cap(s) 110 (also referred to herein as smart cap(s) 110), and the hosted services 308 may comprise a computing system. Thus, the hub 502, cap(s), and hosted services 308 may also include at least a portion of the features discussed in relation to the computing system of the wine inventory device 415. Details regarding the data-holding subsystems of the hub 502, the cap(s) 110, and the hosted services 308 are discussed further herein.

Turning back now to the computing system 415 of a wine inventory device of the wine inventory management system, in at least one example, the data-holding subsystem 413 may include a cap illumination criteria receiving module 402, a wine database update receiving module 408, and a wine inventory management hosted services request module 410. These modules stored within the data-holding subsystem 412 of the computing system 416 may be instructions executable by the logic subsystem 411 to implement the herein described methods and processes.

In one embodiment, the cap criteria receiving module 402 may be configured to receive information regarding criteria for illuminating a cap of the wine inventory management system. For example, the cap illumination criteria receiving module 413 may be configured to receive one or more of a wine request 403 and a cap diagnostic request 405, where the wine request 403 and cap diagnostic request 405 are both criteria for illuminating a cap 110. The wine request 403 may be received via one or more user inputs to a wine inventory application operated on the wine inventory device. For example, the wine request 403 may be received at the cap illumination criteria receiving module 402 via one or more user inputs to conduct a wine search. Example wine searches are described in more detail herein. A cap diagnostic request 405 may also be received at the cap illumination criteria receiving module 402 responsive to one or more user inputs. In at least one example, the cap diagnostic request 405 may be a battery state of charge request.

In such examples where a cap diagnostic request 405 is a battery state of charge request, the cap illumination criteria receiving module 402 may create and send an output to the wine inventory management hosted services request module 410 requesting a battery state of charge update of smart caps in a wine collection. Then the wine inventory hosted services request module 410 may then create and send an output to the smart caps in the wine collection to illuminate their smart caps based upon the state of charge of the battery of the smart cap. Additionally or alternatively, following the wine inventory management hosted services request module 410 sending a request to the wine inventory management hosted services to indicate a battery state of charge of the smart caps in a wine collection, the wine inventory management hosted services may ping the smart caps in the wine collection requesting the state of charge information of the batteries of the smart caps, the smart caps may send their battery state of charge to the wine inventory management hosted services, and the wine inventory management hosted services may send an output to the wine inventory device of the battery state of charge of the smart caps. Then the wine inventory device may indicate the battery state of charge of the smart caps in the wine collection via a display screen of the wine inventory device.

Additionally or alternatively, the data-holding subsystem 413 may further include a wine database update receiving module 408 that is configured to receive information to be communicated to hosted services for updating a hosted wine information database. The cap illumination criteria information may be received by the cap illumination criteria receiving module 402 via a user input, in at least one example. In some examples, the user input may be received via a user interface of the computing system, where the user interface may include any one or combination of a graphical user interface, a microphone for receiving auditory instructions, a mouse, a keyboard, a touch screen, and an optical recognition device. In at least one example, the wine database update receiving module 408 may receive information regarding wine details of a particular wine in a wine collection.

The cap illumination request receiving module 402 and the wine database update receiving module 408 may both be configured to output cap illumination criteria and wine database update information that is received to the wine inventory management system hosted services request module 410. The wine inventory management system hosted services request module 410 may then communicate the cap illumination criteria received at cap illumination criteria receiving module 402 to hosted services 308 (not shown). In at least one example, the wine inventory management hosted services request module 410 may communicate with the hosted services via communication subsystem 420 of the computer system 400 of the wine inventory device of the wine inventory management system. For example, a request may be sent to the wine inventory hosted services via the wine inventory management hosted services request module 410. In one or more examples, the communication subsystem 420 of the computing system of the wine inventory device 415 may communicate with wine inventory hosted services 308 via wireless communication such as Wi-Fi. However, any wireless communication protocol may be possible. For example, in some embodiments the wireless communication may be achieved via Bluetooth low energy (BLE) or near field communication (NFR) wireless communication protocols.

Additionally, in some examples the wine inventory management hosted services request module 410 may communicate with display subsystem 419 of the computer system 400 of the wine inventory device of the wine inventory management system to provide a display summarizing the request being carried out. For example, if a request to illuminate all red wines in a collection was received via the cap illumination criteria receiving module 402, the cap illumination criteria receiving module 402 may output this request to the wine inventory system hosted services request module 410. Then, the wine inventory management hosted services request module 410 may output the request to illuminate all caps associated with red wines to the hosted services of the wine inventory management system via the communication subsystem 420. Additionally, the wine inventory management system hosted services request module 410 may output information regarding the request that was sent to hosted services via the display communication subsystem 420 to the display subsystem 419, and the display subsystem 419 may provide a message of the request made via a display of the wine inventory device (e.g., the display may show a message that a request to illuminate all red wines in the collection was made).

Figure 5A:
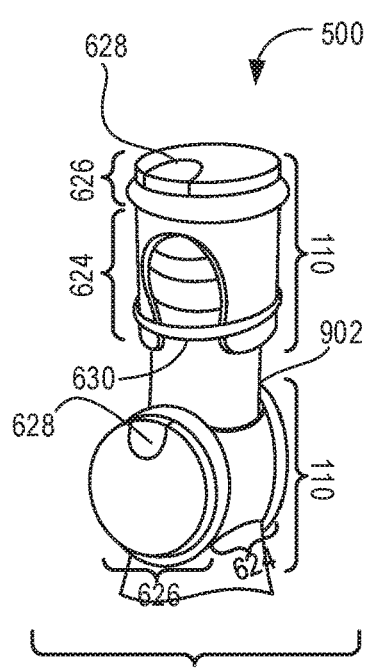
FIGS. 5A-5C show another example smart cap according to at least one embodiment of the present disclosure.
Figure 5B:
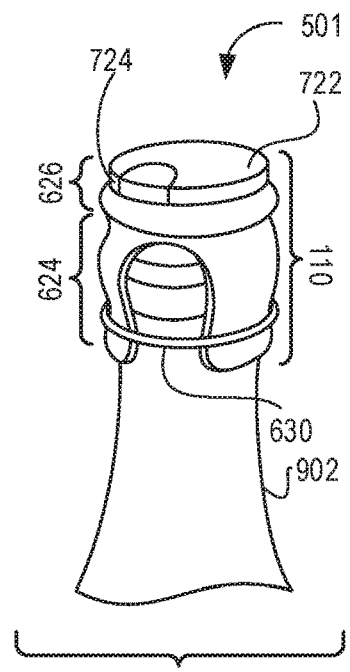
Figure 5C:
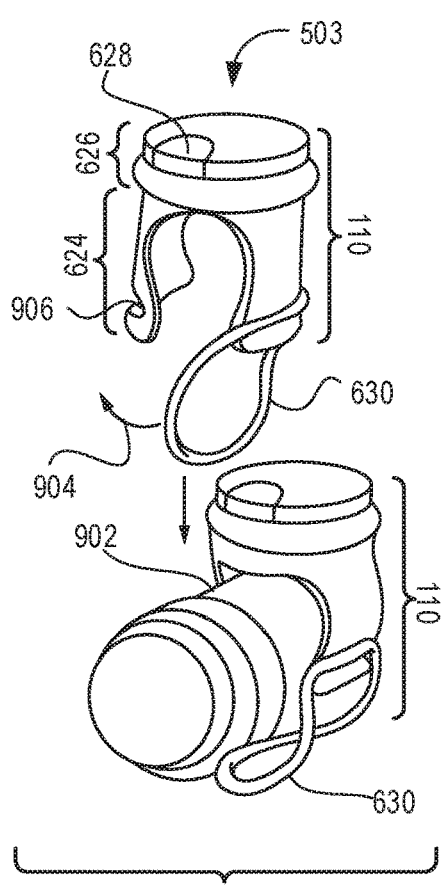

Turning now to FIGS. 5A-5C, FIGS. 5A-5C show views of another example smart cap according to at least one example of the present disclosure, where the another example smart cap may correspond to a smart cap 110 previously discussed. It is noted that the smart cap may also be referenced to as a cap herein.

Turning to FIG. 5A, FIG. 5A shows a first view of the example smart cap 500, where the example smart cap is positioned on a first wine bottle. As shown in FIG. 5A, smart cap 110, may include an indicator portion 626 and a mounting portion 624. Indicator portion 626 may include an indicator light 628. In some examples there may be a single indicator light 628. However, in other examples, indicator portion 626 of smart cap 110 may include a plurality of indicator lights. Indicator light 628 of smart cap 110 may be controlled responsive to user input, as previously described. Mounting portion 624 of smart cap 110 may include a clip 630. Clip 630 may enable a smart cap 110 to be clipped onto a bottle of wine, in some examples. In other examples, however, mounting portion 624 may also enable smart cap 110 to be mounted to other wine containers. Smart cap 110 may include a first opening 632 that may be opposite an indicator portion 626 of smart cap 110. Smart cap 110 may also include a second opening 634 that may be formed in mounting portion 624 of smart cap 110 between clip 630 and indicating portion 626.

The materials of mounting portion 624 and indicating portion 626 of smart cap 110 may be different in some examples. In some examples, mounting portion 624 of smart cap 110 may comprise of a flexible material to accommodate various sized wine bottles. Further, mounting portion 624 of smart cap 110 may have an interior surface and an exterior surface. The interior surface of mounting portion 624 may be a surface of the mounting portion 624 that is in contact with a wine bottle when mounted to the wine bottle. In some embodiments, the interior surface of mounting portion 624 may comprise a non-slip material. This non-slip material may also be spongy, in some examples. An interior surface of mounting portion 624 that comprises a material that is one or more of a non-slip and a spongy material may be advantageous for securing a smart cap 110 to a wine bottle. Indicating portion 626 of smart cap 110 may comprise of a material that less flexible than mounting portion 624.

In some examples, mounting portion 624 and indicator portion 626 of smart cap 110 may be made of the same materials. Smart cap 110 may function as an ultra-low-power sensor and lighting unit. In some examples, indicator portion 626 of smart cap 110 may house a microcontroller that may manage aspects of smart cap 110's functioning. It is noted that the indicator portion 626 of the smart cap 110 housing the microcontroller may be removable in at least one example. The indicator portion 626 housing the smart cap being a removable component may be particularly beneficial, as the indicator portion 626 may be removed to enable recharging of a battery of the smart cap, to service the indicator portion of the smart cap, or to replace the indicator portion of the smart cap. Further details regarding the microcontroller of smart caps 110 may be found at FIG. 7.

In at least one example a height of the smart caps 110 may be varied. For example, smart caps 110 may be increased in height to enable better visibility of indicator lights of the smart caps 110. Further, indicator light(s) 628 of a smart cap 110 may be viewable from an exterior surface of smart cap 110. In some examples, indicator lights 628 of smart cap 110 may be positioned on an indicator portion 626 top surface 722, where top surface 722 of the indicator portion 626 may be an exterior surface of the indicator portion 626 opposite second opening 634 of smart cap 110. In some examples, indicator light 628 of smart cap 110 may also be positioned in surface 724 of smart cap 110, where surface 724 may be a surface indicator portion 626 of smart cap 110 that may be approximately perpendicular to surface 722. In some embodiments, a button may also be positioned in a top surface 722 or a surface 724 that may be perpendicular to surface 722. The button of smart cap 110 may receive a user input. The button of smart cap 110 may be a push button in some examples. Other user input receivers may be possible, however. For example, a capacitive touch based user input receiver may be possible. Moreover, in at least one example, smart cap 110 may receive a user input via a twisting motion of the cap.

In one example, smart cap 110 may be mounted to a wine bottle of a wine collection with an indicator portion 626 of smart cap 110 covering a cap portion of a wine bottle In other examples, smart caps 110 may be mounted to a neck of wine bottles.

In some examples, mounting portions 624 of smart caps 110 may be able to stretch to accommodate the differing diameters of cap/neck portions for bottles. For example, FIG. 5B shows a second view of the example smart cap 501, where the example smart cap is mounted on a wine bottle with a cap and neck that have a greater diameter than the wine bottle shown in FIG. 5A. As shown in FIG. 5B, the mounting portion 624 of the example smart cap stretches to accommodate the greater diameter cap and neck of the wine bottle shown in FIG. 5B. In some examples, smart caps 110 may also be mounted to a neck portion of bottles 902, as shown in FIG. 5A and FIG. 5B. However, in at least one example, the mounting portions 624 of smart caps 110 may be formed of a rigid material that is pushed over the top of the cap portions of the bottle, the rigid material biased such that it squeezes the bottle to firmly mount the smart cap 110 to the bottle.

Turning to FIG. 5C, FIG. 5C shows a third view of the example smart cap 503 being mounted to a neck 902 of a wine bottle. As shown in FIG. 5C, smart caps 110 may include a clip 630 in mounting portion 624 that may hook and unhook from a latch 906. For example, the clip 630 may pivot in a direction as indicated by arrow 904 to transition from the hooked to the unhooked state. Latch 906 may be a part of mounting portion 624. Latch 906 may be a notch formed into mounting portion 624 of smart caps 110 in some examples. Clip 630 of smart caps 110 may be unhooked from latch 906 to position a smart cap over a neck portion of a wine bottle. Then, after the neck portion of the wine bottle is positioned within an opening of the smart cap, the clip 630 may then be hooked into latch 906. Clip 630 may be formed of an elastomer material in some examples. However, other materials may be possible. In other examples, a clip 630 may be left hooked into latch 906, and a cap portion of a wine bottle may be positioned within the opening without needing to unhook clip 630 from latch 906. In some examples, a smart cap 110 may partially cover a cap portion of a wine bottle. In other examples, however, a smart cap may not cover any of a cap portion of a wine bottle.

In addition to the indicator portion 626 of the smart cap 110 including one or more indicator lights 628, in some examples one or more sensors for receiving a user input may be housed in the indicator portion of the smart cap 626. For example, an accelerometer sensor may be housed in smart cap 110. While, the smart cap shown in FIGS. 5A-5C includes a single indicator light, it is noted that any of the smart caps discussed herein may have an indicator portion where the indicator lights are arranged in a ring, as opposed to a single light or linearly arranged lights. Examples where the indicator portions of the smart caps include indicator lights arranged in a ring on the smart cap may be particularly beneficial for enabling easy viewing of the smart cap when the smart cap is illuminated. The ring of indicator lights may be formed into one or both of a top surface of the smart cap and a side surface of the smart cap, for example.

In embodiments where a user input is received via an accelerometer sensor, a user input may include positioning a bottle of wine from a first position to a second position while the smart cap that includes the accelerometer sensor is mounted to the wine bottle being positioned. An accelerometer sensor positioned in smart cap 110 of the wine bottle may detect the change in positioning and communicate the change in position to a hub system of the wine inventory management system. Responsive to the communication, the hub system may then communicate with one or more of a wine inventory application and wine inventory hosted services of the wine inventory management system, and an output may be created. For example, the output may include a message being displayed via a wine inventory application or may include indicator lights of the smart cap 110 may be illuminated. In other examples where an accelerometer sensor in smart cap 110 is used to receive a user input, smart cap 110 may not communicate with a hub system responsive to user input and smart cap 110 may instead illuminate indicator lights responsive to the user input without first communicating with a hub system of the wine inventory management system.

Turning now to FIG. 6, isometric views 600 of various example smart caps 601, 603, 607 are shown. Each of the various smart caps 601, 603, 607 include an indicator portion 1206 and a mounting portion 1202. Mounting portion 1202 is a C-shaped clip including an open portion 1208 opposite a closed portion. Mounting portion 1202 may fit over a neck portion or a cap portion of a wine bottle. At least a portion of an inner surface 1210 of the mounting portion 1202 may comprise a gripping material to create a better coupling between the mounting portion 1202 and a wine bottle and to the protect the wine bottle (e.g., the wine bottle neck or wine bottle cap) from damage. In at least one example, the inner surface 1210 may comprise cork. However, in other examples, the inner surface 1210 may comprise a rubber. Indicator portion 1206 may include an indicator light 1204. The indicator light 1204 may be varied in size. For example, as shown in smart cap 601, the indicator light 1204 may only extend for a portion of a side surface of the mounting surface 1202, whereas in other examples, such as smart cap 603, the indicator light 1204 may extend to the inner surface 1210 of the smart cap. Moreover, the indicator light 1204 may be integrated with the mounting portion 1202, such as shown in smart caps 601 and 603, or the indicator light 1204 may be a part of an indicator portion 1204 that is detachable, such as shown in smart cap 607. In some examples, indicator portion 1206 may include a plurality of indicator lights. As discussed above, the indicator lights may be in a ring formation to enable better viewing. Further, in at least one example, the mounting portion that is a C-shaped clip may comprise multiple C-shaped clips aligned vertically with one another. Thus, multiple C-shaped clips of a mounting portion may fit over a neck portion of a wine bottle. Moreover, though the indicator portion 1206 positioned such that the indicator portion 1206 may not cover a cap of a wine bottle upon mounting the mounting portion 1202 to a neck of a wine bottle, in at least one example, the indicator portion 1206 may be positioned at an end of the C-shaped clip 1202 mounting portion 1202, such that the indicator portion 1206 may cover a wine cap upon coupling the smart cap 110 to the wine bottle. Further, the indicator portion 1206 may be detachable in at least one example, and the indicator portion may include the microcontroller and one or more environmental sensors therein.

Further, in regards to manufacturing the smart caps, there are several different manufacturing methods that may be possible.

For example, a smart cap may be produced via a first example manufacturing method which includes a co-molded construction of a smart cap. A co-molded construction may include tooling that adds cost to construction. A co-molded manufacturing method to create a smart cap that may utilize a centralized light pipe may make it easier illuminate smart cap via a single LED. However, there may be compromised side visibility of LED lights when forming a smart cap via co-molded construction.

In another example, a smart cap may be produced via a second example manufacturing method which includes forming a dedicated button and then using co-molded construction for the remainder of the smart cap. Forming a dedicated button and then using co-molded construction for the remainder of the smart cap may enable use of a loop style light pipe. Loop style light pipes may require multiple LEDs for adequate brightness, however, there may be minimal hotspots. Side visibility of LEDs in the second example manufacturing method is improved over the first example manufacturing method. However, side visibility of LEDs using the second manufacturing method may still be compromised.

In a further example, a smart cap may be produced via a third example manufacturing method which comprises a single body construction. A single body construction eliminates the need for additional co-molding tools. A light pipe design in a single body construction may be more complex to engineer, however. In a single body construction of a smart cap, a loop style light pipe may require multiple LED lights for adequate brightness and minimal hot spots. A single body construction manufacturing method for smart cap may result in the best top and side LED visibility.

Smart caps that may be formed via a first, co-molding manufacturing method may comprise satin finished co-molded polycarbonate, in at least one example. However, other materials may be possible. In some examples, a mounting portion of smart cap may comprise a one piece satin finish co-molded thermoplastic elastomer. Other materials that enable flexibility may be used for mounting portions of smart caps in other examples. Further, in at least one example, a rigid material may be used to form the mounting portion of the smart caps.

The smart caps may be manufactured to include a microcontroller. For example, the smart caps may include a microcontroller in the indicator portion of the smart cap, and the indicator portion may be detachable to enable easy replacement of the indicator portion. The microcontroller may be a circuit board in some examples. Further, the smart cap may be battery operated. In some examples, a battery of a smart cap may be a CR2450 lithium battery. A smart cap may also include a battery cover. Indicator light and button, microcontroller, battery, and battery cover may be housed in an indicator portion of a smart cap in some examples. This indicator portion of the smart cap comprising the indicator light and button, microcontroller, battery and battery cover may be removable from a mounting portion of the smart cap. The indicator portion be removable may be advantageous to enable fast replacement of faulty smart caps, for example. In some examples, smart cap may house an RFID antenna for communicating with a hub system of the wine inventory management system as a part of the communication subsystem of the smart cap.

In another example manufacturing method, smart caps may be manufactured via forming a dedicated button and then using co-molded construction for the remainder of the smart cap and smart cap to be manufactured via forming the smart caps with a single body construction. Further, in some manufacturing examples, the frosted acrylic light pipe may be sonic welded to a body of the smart cap.

In some examples, a body of smart cap may be formed in a single piece and a button of smart cap may be formed separately. A body of smart cap may be made from an elastomeric material in some examples. However, in some examples, a smart cap may not comprise a button and may instead receive a user input through a twisting motion of the smart cap, for example.

The microcontroller of the smart caps may manage aspects of smart cap functions. The microcontroller may be a circuit board. The microcontroller may be contained in a detachable housing of the smart cap.

Figure 7:
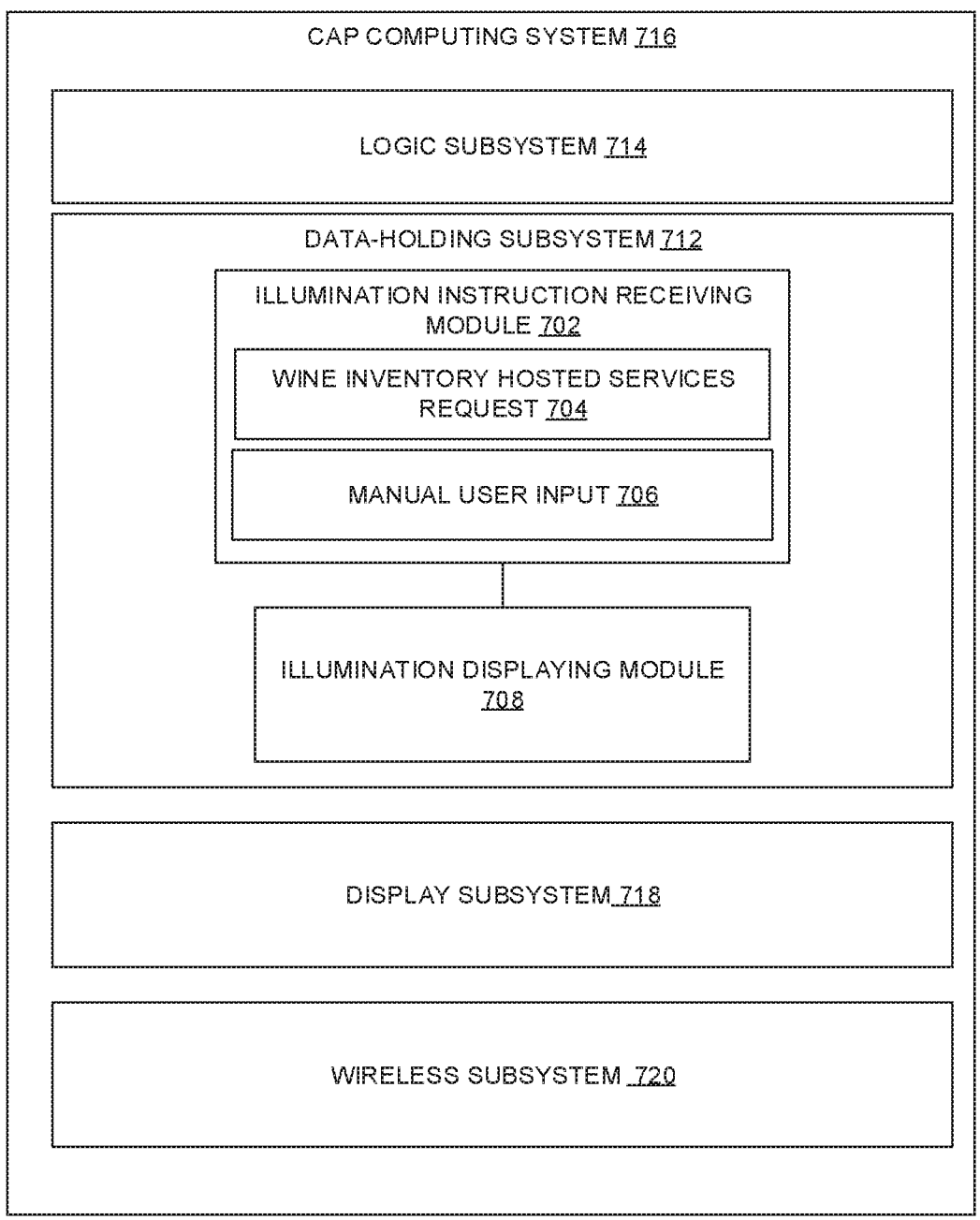
FIG. 7 shows a block diagram of an example computing system of a smart cap of the wine inventory management system according to at least one embodiment of the present disclosure.

Turning now to FIG. 7, a block diagram of an example computing system of a cap 700, where the microcontroller of the cap is the computing system of the cap, is shown. In some examples, cap computing system 716 may comprise a data-holding subsystem 712, where the data-holding subsystem 712 includes an illumination instruction receiving module, an illumination displaying module, and an environmental output receiving module. Illumination instruction receiving module 702 may receive instructions such as a wine inventory hosted services request 704 or a manual user input 706 to control lighting of one or more indicator lights of the smart cap, such as an LED lighting ring through software PWM control. For example the illumination instruction receiving module 702 may receive instructions from the wine inventory management system, then the illumination instruction receiving module 702 may send an output to an illumination displaying module 708 of the data holding subsystem 712. The illumination display module 708 may then illuminate the one or more indicator lights via display subsystem 718, which communicates with the one or more indicator lights, such as an LED board. In examples where the smart cap may be an LET lighting ring, the LED lighting ring may include a plurality of indicator lights that may be positioned on an exterior of smart cap. In some examples, the LED lighting ring may include a plurality of indicator lights covered by a transparent or translucent material.

Cap computing system 716 may also manage a wireless subsystem 720 (i.e., communication subsystem) of the smart cap. Cap computing system 716 management of the wireless subsystem may include management of a radio configuration and communication of smart cap (e.g., communication of a smart cap with a hub system) in some examples. For example, the wireless subsystem 720 may be used to communicate environmental sensor output to wine inventory hosted services. Additionally, in some examples, the wireless subsystem 720 may be used to receive illumination requests from the wine inventory hosted services. Cap computing system 716 may also optimize operation of a battery through deep sleep modes.

In some embodiments, cap computing system 716 may be coupled to environmental sensors. Environmental sensors may be used for environmental sensing (e.g., temperature, humidity, barometric pressure, accelerometer readings at the wine bottle, etc.). In some examples, the communication subsystem 720, which may be a wireless subsystem, may be a Bluetooth Low Energy (BLE) wireless subsystem. In other examples, the wireless subsystem may utilize radio technology, such as radio frequency identification (RFID). It is noted that if cap computing system 716 communicates with a hub system utilizing any one of BLE, RFID, communication subsystem 720 may include an RFID antenna.

In examples where smart cap includes a button, cap computing system may be configured to receive a manual user input 706. The manual user input 706 may include pressing of the button of the smart cap, for example. Pressing of the button of the smart cap may cause a signal to be created in the cap computing system 716. The cap computing system may then communicate with one or more of a wine inventory application and wine inventory hosted services via a hub responsive to the button receiving the manual user input 706. In one example, responsive to the button receiving a user input, all indicator lights of smart caps associated with wines similar to the wine associated with smart cap may be illuminated. Similarly, a manual user input 706 may be received via a twisting motion of the smart cap.

In examples where smart cap associated with the cap computing system 716 does not include a button, an accelerometer sensor may receive a user input. In examples where an accelerometer sensor is used to receive a user input, the user input may include repositioning a wine bottle. For example, the user input may include positioning of a bottle of wine from a first position to a second position while the smart cap that includes the accelerometer sensor is mounted to the wine bottle being positioned.

An accelerometer sensor positioned in the smart cap of the wine bottle may detect the change in positioning and communicate the change in position to a hub system of the wine inventory management system. Responsive to the communication from the cap computing system 716 to the hub system, the hub system may then communicate with one or more of a wine inventory application and wine inventory hosted services of the wine inventory management system, and an output may be created. For example, the output may include a message being displayed via a wine inventory application or may include sending a wine inventory hosted services request 704 to illuminate indicator lights of one or more smart caps. In other examples where an accelerometer sensor in smart cap 110 is used to receive a user input, smart cap 110 may not communicate with a hub system responsive to manual user input 706 and smart cap 110 may instead illuminate indicator lights responsive to the user input without first communicating with a hub system of the wine inventory management system.

Further, it is possible in at least one embodiment that the wine inventory hosted services request 704 may be a query for environmental sensor output of the sensors of the smart cap. For example, the wine inventory hosted services may request the output of the environmental sensors of the smart cap responsive to a user input (e.g., via the wine inventory application) or the wine inventory hosted services may request the output of the environmental sensors of the smart cap periodically by sending a request to the cap computing system 716 of one or more smart caps via the communication subsystems 716 of the one or more smart caps. Then, responsive to the one or more smart caps receiving the request for the output of the environmental sensors, the one or more smart caps may send the output of the one or more environmental sensors to the wine inventory hosted services. Then the wine inventory hosted services may use the output from the environmental sensors in order to calculate a wine condition of one or more wines in the wine collection, for example.

Regarding the hardware aspect of the smart caps, in some embodiments, a single smart cap may house a microcontroller that comprises two circuit boards. In examples where the microcontroller comprises a two circuit board arrangement, the microcontroller may comprise a first circuit board and a second circuit board. A battery may be positioned between the first circuit board and the second circuit board, in embodiments where the microcontroller comprises two circuit boards. Further, smart caps that include a microcontroller with a two circuit board arrangement may also include a second button.

The second button may be positioned below second circuit board, where second circuit board is positioned between a battery and second button, in some examples. Embodiments that include second button may be advantageous for sensing when smart cap has been mounted for a wine bottle, as mounting the smart cap to the bottle will compress the second button. In some examples, responsive to the second button receiving an input, the smart cap may communicate via a hub system of the wine inventory management system to indicate that smart cap has been mounted to a wine bottle. In some examples, the communication with the hub system that smart cap has been mounted to a wine bottle may be communicated to one or both of the hosted services and a wine inventory application of the wine inventory management system. For example, in embodiments that include second button, mounting a smart cap to a bottle may cause second button to be pressed. The second button being pressed may cause a signal to be created in second circuit board. Then, responsive to receiving input via second button, the second circuit board may communicate with a hub system of the wine inventory management system.

The second button may also be advantageous for detecting the removal of a smart cap from a wine bottle. For example, removing the smart cap from a wine bottle may cause the second button to transition from a first state to a second state. The first state may be a state where second button is receiving an input (e.g., being pressed), and the second state of second button may be a state when second button is not receiving an input. Responsive to the second button transitioning from the first state to the second state, the microcontroller may communicate with a hub system to indicate smart cap has been removed from a wine bottle. In at least one example, detection of removal of a smart cap from a wine bottle may automatically remove a bottle from an inventory via the wine inventory application and the wine inventory hosted services. Thus, an accurate wine inventory may be more easily maintained. It may then be communicated that the smart cap has been removed from a wine bottle to one or more of a wine inventory application and wine inventory hosted services of a wine inventory management system responsive to second button transitioning from the first state to the second state. It is noted that in at least one embodiment, the second button may be transitioned between the first state and the second state due to a twisting motion of the smart cap.

As far as enabling the cap computing system 716 to communicate with the wine inventory hosted services via a hub system, in some examples, a pairing sequence may need to be performed in order to pair a smart cap 110 with a hub system. Alternatively, however, the smart caps 110 may instead be pre-provisioned. Put another way, in at least one embodiment, the smart caps 110 may instead be pre-provisioned to be associated with a particular hub system such that upon ordering and receiving a wine inventory management system, the smart cap(s) and hub(s) received are already paired. Thus a pairing sequence to pair a smart cap 110 with a hub sequence may not be necessary in such examples where the smart caps 110 may be pre-provisioned.

However, in embodiments where the smart cap 110 may need to undergo a pairing sequence to pair the smart cap 110 with a hub system. Furthermore, in at least one example, a pairing sequence may be necessary to pair a smart cap 110 to a wine inventory device, where the wine inventory device may be as a mobile device, for example. Smart cap 110 may include any one of the example smart caps previously described. The pairing sequence may be for pairing a smart cap 110 with another type of wine inventory device via a wireless communication link, in some examples.

The pairing sequence may be initiated responsive to a smart cap 110 receiving a user input. The user input may be a pressing and holding button of smart cap 110. In some examples, user input may include pressing and holding a button of a smart cap 110 for at least a threshold amount of time. For example, the threshold amount of time may be two seconds.

An indicator light of smart cap 110 may be illuminated responsive to a pairing sequence being initiated. The indicator light may be illuminated in different colors or light animation patterns corresponding to a status of the pairing sequence. The statuses of a pairing sequence may include one or more of initiation of a pairing sequence, pairing success, and pairing failure. For example, indicator light(s) of smart cap 110 may flash when a pairing sequence is initiated. In other examples, indicator light(s) of smart cap 110 may be illuminated in a particular color when the pairing sequence is initiated. Following initiation of a pairing sequence, the smart cap 110 may attempt to establish a communication link with another wine inventory device. A pairing success may be when a smart cap 110 successfully establishes a communication link with another wine inventory device. In some examples, the wine inventory device that a smart cap 110 attempts to pair with may be hub of a hub system. A pairing failure may be when a smart cap 110 fails to establish a communication link with a hub system hub for greater than a threshold amount of time following initiation of a pairing sequence. Following pairing success or pairing failure, a pairing sequence may end.

Figure 8:
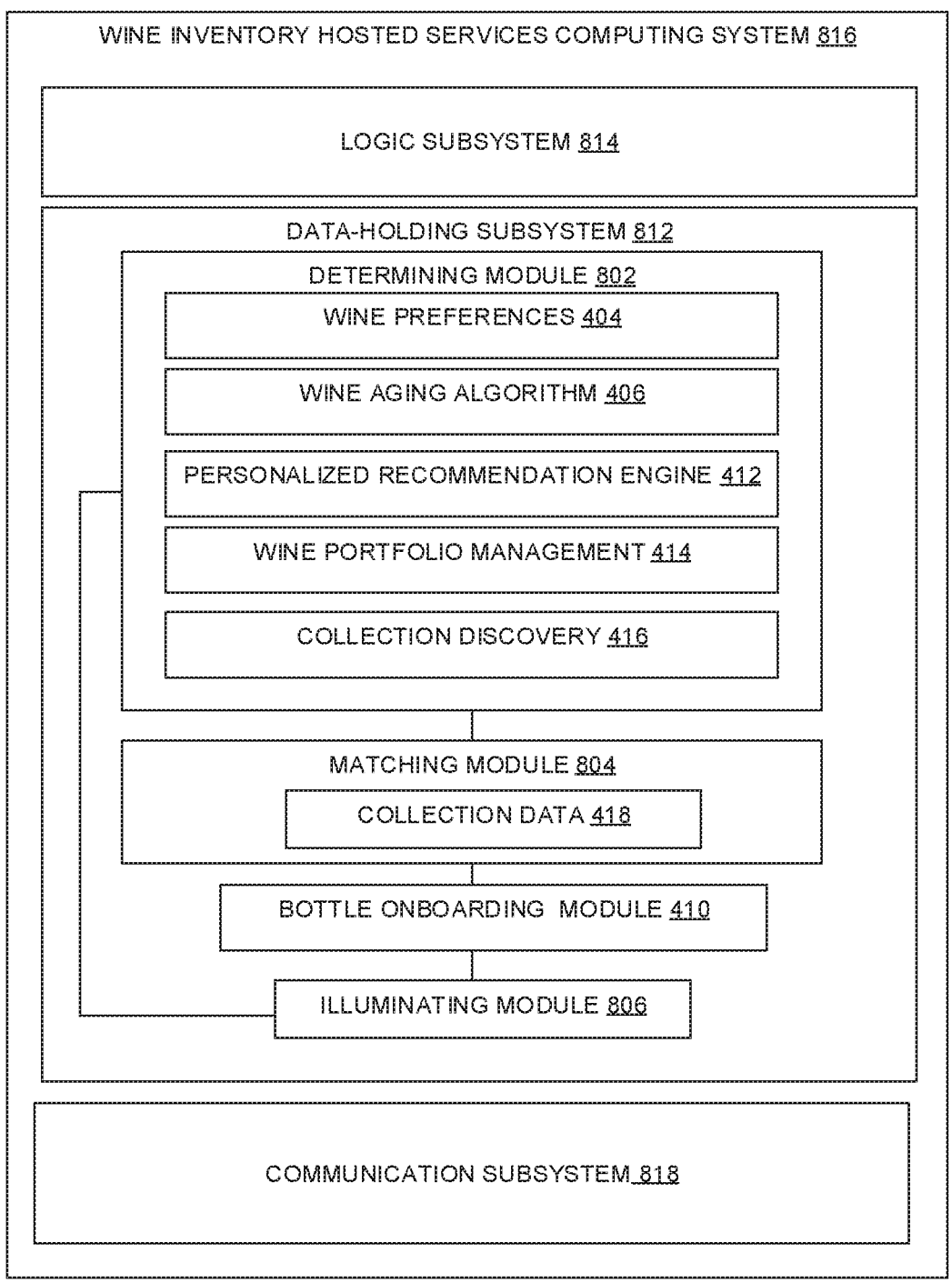
FIG. 8 shows a block diagram of an example computing system of the wine inventory hosted services of the wine inventory management system according to at least one embodiment of the present disclosure.

Turning now to FIG. 8, a block diagram 800 of a wine inventory hosted services computing system 816 is shown. As shown in FIG. 8, it is noted that the wine inventory hosted services computing system 816 includes several elements similar to the computing system of wine inventory device 416 described at FIG. 4. In particular, the logic subsystem 814, data-holding subsystem 812, and communication subsystem 820 of the wine inventory hosted computing system 816 are very similar to the logic subsystem 411, data-holding subsystem 413, and communication subsystem 420, respectively, with the exception of the specific modules included in the data-holding subsystem 812. Thus, elements described in relation to these components of FIG. 4 may apply to the wine inventory hosted services computing system 816. Details regarding the data-holding subsystem 812 are provided herein.

Regarding data-holding subsystem 812 of the wine inventory hosted services computing system 816 may comprise a determining module 802, a matching module 804, an illuminating module 806, and a bottle onboarding module 808. The modules of wine inventory hosted services may create outputs responsive to one or more inputs of a user input via a wine inventory application (e.g., a user wine search), environmental sensor output of the smart caps, and a user input received by a button of the smart cap (e.g., pressing of the button). These one or more inputs may be received via a communication subsystem 818 of the wine inventory hosted services computing system 816, in at least one example. Some or all of the functions described as being carried out by the modules and sub-modules of wine inventory hosted services may be included in an example wine inventory management system.

The illuminating module 806 may illuminate smart caps 110 or create a display via wine inventory application 310 responsive to an output from a determining module 802 and a matching module 804. For example, responsive to receiving an output from the determining module 802, the illuminating module 806 of the wine inventory hosted services computing system 806 may communicate via communication subsystem 818, which may be a wireless communication subsystem, to send an illumination request to a smart cap. Responsive to the smart cap receiving the illumination request, a microprocessing unit of the smart cap may control one or more lights of the smart cap to illuminate the smart cap in accordance with the request from the wine inventory hosted services computing system. For example, the illumination request may include a particular color, brightness, light animation pattern, etc., and the microcontroller of the smart cap may illuminate the smart cap in accordance with the request by controlling one or more lights of the smart cap. The illuminating module 806 may send multiple illumination requests to different smart caps or a same illumination request to multiple smart caps in at least one embodiment. Further, it is noted that in at least one example, the illumination request may be a request to cease illuminating a smart cap that is already illuminated. In another example, the illuminating module 806 may provide a display on a wine inventory device operating the wine inventory application responsive to receiving an output via the determining module 802.

The determining module 802 may create an output to send to the illuminating module 806 based on user input and one or more outputs received from the sub-modules. The user input may be user input into a wine inventory application. For example, a user may perform a particular wine search via the wine inventory application, the wine inventory application may communicate the results of the search to the wine inventory hosted services, and the wine inventory hosted services may then send an illumination request to one or more smart caps in accordance with the search results. Additionally or alternatively, the user input may be a request to illuminate a particular wine received via the wine inventory application. The wine inventory application may then communicate the request to illuminate the particular wine to the wine inventory hosted services, and the wine inventory hosted services may then send an illumination request to one or more smart caps based on the request that the wine inventory hosted services received from the wine inventory application. Moreover, in another example, the determining module 802 of wine inventory hosted services 308 may include a wine preferences sub-module 404 for maintaining a user's wine drinking preferences. For example, wine preferences sub-module 404 may maintain a history of a user's wine selections and wine ratings to create a profile of a user's wine preferences. Thus, in some examples, a wine inventory application may receive a request from a user to provide a wine recommendation, and the wine inventory application may communicate this request for a wine recommendation to the wine inventory hosted services.

The wine inventory hosted services may then utilize the wine preferences sub-module 404 and, in some cases, the matching module 804 to determine a wine recommendation, and then the wine preferences sub-module 404 may a send an illumination request to one or more smart caps to illuminate the smart caps, and thus the wine(s), that are recommend.

The determining module of wine inventory hosted services 308 may also include a wine aging algorithm sub-module 406. Wine aging algorithm sub-module 406 may take into consideration a wine's characteristics and models for various parameters that affect aging to generate information related to the aging of wines in a wine collection. For example, wine aging algorithm sub-module 406 may take into account one or more of environmental conditions, information about a wine, and an amount of time a wine has been bottled create an output. In some examples, environmental conditions may be based on environmental sensor output of smart caps to track environmental conditions that may impact aging (e.g., temperature, pressure, ambient light). It is noted that the environmental sensor output of the smart caps may be received via communication subsystem 820 in at least one example. In some examples, wine aging algorithm module 406 may take into account characteristics of a wine that may impact a wine's peak drinking age (e.g., pH, tannin content, alcohol level, residual sugar, etc.). Based on an output from wine aging algorithm sub-module 406, an indication may be created to indicate a condition of the wine. The indication may be illumination of smart caps associated with the wine for which the output was created, in some examples. The smart caps may be illuminated by illuminating indicator lights of the smart caps via the illuminating module. In other examples, the indication may be a message displayed via wine inventory application 310.

Indicator lights of smart caps may be illuminated with particular colors and in particular patterns to convey specific messages. For example, there may be an indicator light color code for indicating particular wine conditions calculated via the wine aging algorithm sub-module 406. These wine conditions may include one or more of a holding condition, a not yet peaked condition, a drink now condition, a past peak condition, and an in decline condition.

A holding condition may be indicated responsive to determining that a wine needs to be held for more than a threshold period of time before the wine is in peak condition. In some examples, a holding wine condition may be indicated by illuminating indicator lights of smart caps in red.

A not yet peaked condition may be indicated responsive to determining that a wine needs to be held for less than the first threshold period of time before the wine is in peak condition. In some examples, a not yet peaked condition may be indicated by illuminating indicator lights of smart caps in purple.

A drink now condition may be indicated responsive to determining that a wine is in peak condition. A drink now condition may be indicated by illuminating indicator lights of smart caps in green in some examples.

A past peak condition may be indicated responsive to determining that a wine has been held past a peak condition for less than a second threshold period of time. A past peak condition may be indicated by illuminating indicator lights smart caps in yellow in some examples.

An in decline condition may be indicated responsive to determining that a wine has been held past a peak condition for more than the second threshold period of time. In some examples an in decline condition may be indicated by illuminating indicator lights of smart caps in blue.

In other examples, indicator lights of a smart cap may be illuminated in a particular color for indicating the drinkability of a wine. For example, indicator lights of smart caps may be illuminated in green to indicate that wine is in a ready to drink condition. In other embodiments, other colors may be associated with a wine being ready to drink. The determination of whether or not a wine is ready to drink may also be determined via the wine aging algorithm sub-module 406.

The condition of a wine may be a current condition of the wine relative to a peak condition of the wine. For example, conditions of the wine may include that the wine needs to be held to reach peak condition, that the wine is in peak condition, or that the wine is past peak condition. The condition of a wine may also be a drinkability of a wine. For example, based on an output from wine aging algorithm sub-module 406, a wine may be indicated as too young, ready, or too old to drink.

The lights to indicate a wine condition may be color coded. For example, each condition of a wine being too young, ready, or too old to drink may be indicated via illuminating smart caps in a different color for each condition. In other examples, the lights to indicate that the wine is ready to drink may be a first color, while the lights to indicate that a wine is too young or too old to drink may be a second color.

In some examples, wine aging algorithm sub-module 406 may create an output to the illuminating module or the matching module responsive to a user input. In other examples, wine aging algorithm sub-module 406 may create an output to one or more of smart caps 110 and wine inventory application 310 responsive to exceeding a threshold time since a last update of a wine's condition.

Wine aging algorithm sub-module 406 may create an output and compare that output with a matching module before creating an indication via wine inventory application 310 or illuminating smart caps 110 via the illuminating module 806. For example, the matching module may comprise a collection data sub-module 418. Collection data sub-module 418 may include threshold values to which the wine aging algorithm sub-module 406 may compare an output in order to determine the drinkability of a wine. In other examples, however, aging indicators sub-module 408 may include threshold values for which the wine aging algorithm module 406 may compare an output to in order to determine a wine's drinkability.

The determining module may further include an aging indicators sub-module 408 that may store information used in wine aging algorithm sub-module 406 to calculate a wine's drinkability. For example, aging indicators sub-module 408 may store information regarding one or more of technical information about a wine (e.g., pH, tannin content, alcohol level, residual sugar, etc.), an amount of time since a wine was bottled, and environmental conditions to which that wine has been exposed. A set of information in aging indicators sub-module 408 (e.g., information about a wine, amount of time since a wine was bottled, environmental conditions) may be associated with a smart cap 110 of a cap display 306. The set of information in aging indicators sub-module may be received from a winery user via wine inventory application 310 in some examples. In another example, information about a wine such as pH, tannin content, alcohol level, or residual sugar may be added during a wine onboarding process, responsive to querying a wine database of the matching module. In some examples, the wine database is included in collection data sub-module 418, and the information in the wine database may be received from winery users.

Bottle onboarding module 410 may include bottle onboarding logic that eases the process of adding new wines to a wine inventory management system. In some examples, the bottle onboarding logic of bottle onboarding module 410 may enable the addition of wine to a wine collection responsive to a user input. For example, the bottle onboarding logic may include an automated wine lookup algorithm that is initiated responsive to the user input. In some examples, an image of a wine bottle label may be the user input. In other examples, however, the user input may be a voice command or a manual input.

In embodiments where the user input is an image of a wine bottle label, the image of the wine bottle label may be captured via a camera of wine inventory device 302. The image of the wine bottle label may be provided to wine inventory application 310, and bottle onboarding module 410 may access the wine bottle label image via wine inventory application 310. After a wine bottle label image is inputted, bottle onboarding module 410 may infer wine specifics from the image of the wine bottle label via optical character recognition (OCR).

In embodiments where the user input is a voice command, wine inventory device 302 may receive the voice command, and voice recognition technology may be used to determine the meaning of the voice command. For example, a voice command may be a voice command to initiate a bottle onboarding process and to provide information about a wine that is to be added to a wine collection.

In examples where the user input is a manual input, wine inventory application 310 may receive the manual input via a user interface of wine inventory device 302. However, in other examples where the user input is a manual input, a smart cap 110 of the wine inventory management system may receive the user input.

In some embodiments, a combination of the types of user inputs may be used to add a wine to a wine collection via bottle onboarding module 410. For example, one or more of a wine bottle label image, voice command, and a manual input may be used to add a wine to a wine collection. In other embodiments, however, a single type of user input may be used to add a wine to a wine collection via bottle onboarding module 410. Once a wine is added to a wine collection, the wine that has been added to the collection may be added to wine portfolio management sub-module 414.

Bottle onboarding module 410 may include an automated wine lookup algorithm that can search for data within known data sources to populate the inventory database automatically. In some examples, the known data source may be data stored in collection data sub-module 418 of the matching module. The data stored in collection data sub-module 418 may be a wine database, for example. The bottle onboarding module 410 may initiate the automated wine lookup algorithm responsive to the user input. In some examples, the user input to initiate the automated wine lookup algorithm may be one or more of the user inputs discussed above.

The determining module may further include a personalized recommendation engine sub-module 412 that may also be included in wine inventory hosted services 308. In some examples, the personalized recommendation engine sub-module 412 may suggest wine purchases based one or more of past consumption habits, personal preferences, recommendations, or market data. Information used for the personalized recommendation engine sub-module 412 may be stored in collection data sub-module 418, for example. Personalized recommendation engine sub-module 412 may create a recommendation responsive to input of user. In some examples, personalized recommendation engine sub-module 412 may create a recommendation responsive to exceeding a threshold time since creating a last personalized recommendation. Personalized recommendations may be displayed via wine inventory application 310 on wine inventory device 302. Further, in at least one example, smart caps of wines in a wine collection that are recommended as determined by the personalized recommendation engine sub-module 418 may be illuminated. In some examples, the personalized recommendation engine sub-module 418 may illuminate smart caps in a particular pattern to convey a message of recommended ranking.

In one example, wine rankings for the top three wines may be associated with specific indicator light patterns. For example, a wine that has a top ranking may be indicated by illuminating one-third of an indicator light ring of a smart cap. A wine that has a second place ranking may be indicated by illuminating two-thirds of an indicator light ring of a smart cap. A wine that has a third place ranking may be indicated by illuminating the entire indicator light ring of a smart cap. In other examples, other lighting patterns may be used. Various other light animation patterns may also be associated with different wine rankings.

The matching module may further include wine portfolio management sub-module 414 which may also be included in wine inventory hosted services 308. Wine portfolio management sub-module 414 may enable a user 402 to view and organize wines in a wine collection. In some examples, wine portfolio management sub-module 414 may enable removal of wines from a wine collection. The removal of the wines may be responsive to input from user 402. In some examples, if a wine collection is stored at multiple locations, wine portfolio management sub-module 414 may communicate with wine inventory application 310 to display which wines may be at which locations via the wine inventory application 310. In another example, wine portfolio management sub-module 414 may organize a wine collection by categories such as varietal, region, year, or winery. Other categories may be possible. Information about the wines and their locations for wine portfolio management sub-module 414 may be stored at collection data sub-module 418 and in some examples.

The determining module may further comprise a collection discovery sub-module 416 that may suggest wines to be added to a current wine collection. For example, a profile may be created for a wine collection based on information about the wines in the wine collection, then collection discovery sub-module 416 may make recommendations based on the created profile of the wine collection. In some embodiments, a collection discovery sub-module 416 may create an automated purchase or purchase recommendation based on an aggregation of user feedback, collection state, and data from suppliers and/or wineries. These recommendations may be displayed via wine inventory application 310.

Figure 9:
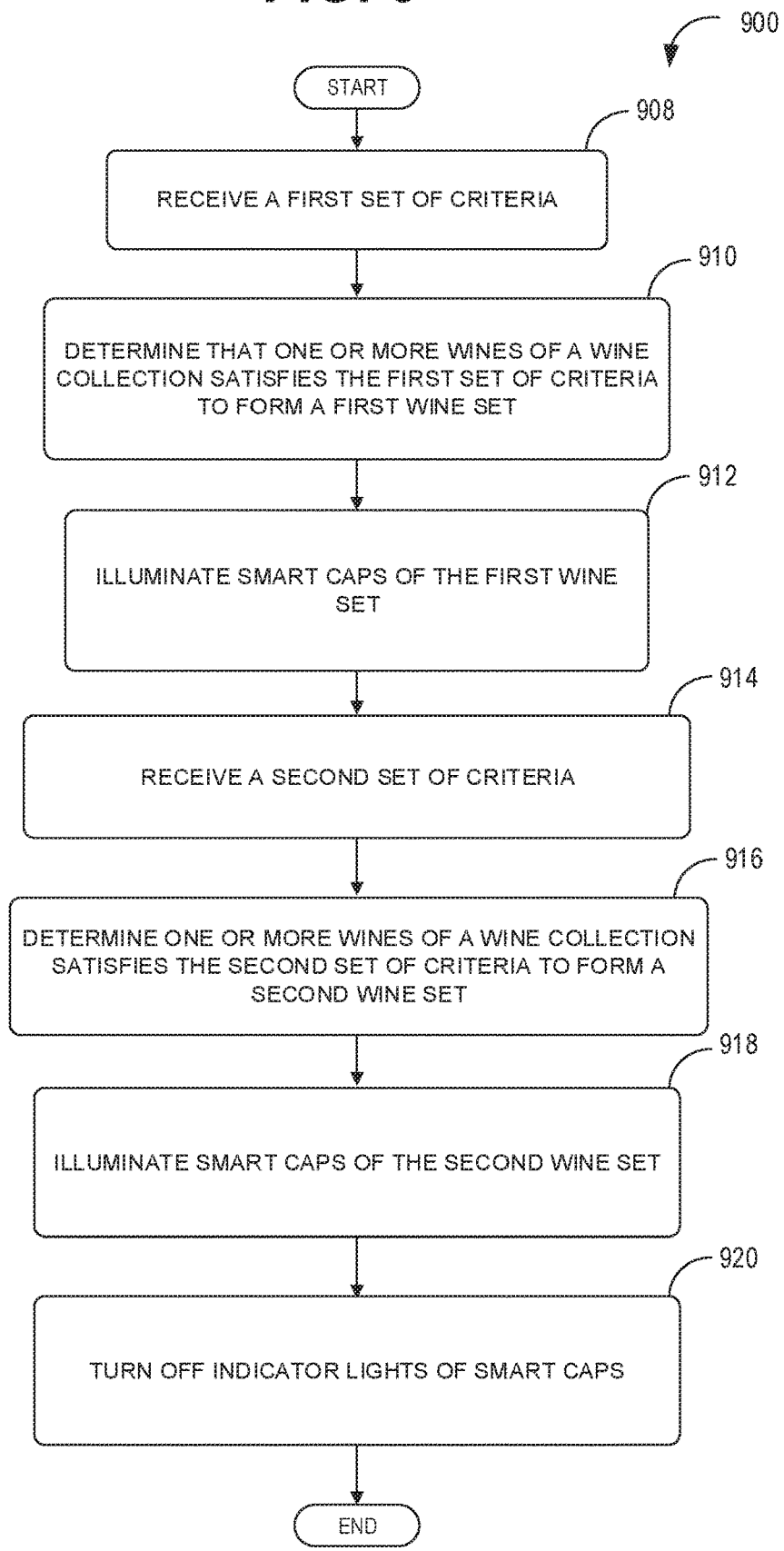
FIG. 9 shows an example flow chart of a first example method according to at least one embodiment of the present disclosure.

Turning now to FIG. 9, a flow chart of an example method 900 according to at least one example of the present disclosure is provided.

Step 908 of method 900 may include receiving a first set of criteria. The first set of criteria may be any one or combination of the criteria described herein as a result of a wine search or a diagnostic request, for example. The first set of criteria may be received via a user input, such as an input into a wine inventory application of a wine inventory device. For example, the first set of criteria may be results from a wine search performed via the wine inventory application, for example. Other requests such as a request for a wine recommendation and a request for a particular wine to be illuminated may be received via a user input into the wine inventory application. The first set of criteria may be communicated to the wine inventory hosted services, so that the wine inventory hosted services may receive the first set of criteria.

Following receiving the first set of criteria at step 908, step 910 may include determining that one or more wines of a wine collection satisfies the first set of criteria to form a first wine set. In at least one example, the one or more wines are determined to satisfy the first set of criteria to form the first wine set via the wine inventory hosted services. For example, in cases where the first set of criteria received at the wine inventory application is communicated to the wine inventory hosted services, and the wine inventory hosted services may process the first set of criteria received at the wine inventory application to determine that one or more wines of a wine collection satisfies the first set of criteria to form the first wine set. The wine inventory hosted services may process the first set of criteria via one or both of the determining module and the matching module of the wine inventory hosted services computing system. For example, any of the examples discussed above in regards to one or more of the determining module and the matching module processing information to form an output to send the illuminating module of the wine inventory hosted services computing system may be possible.

After determining that one or more wines of the wine collection satisfies the first set of criteria to form the first wine set, method 900 includes illuminating smart caps for the first wine set at step 912. Illuminating the smart caps that satisfies the first set of criteria may include sending an illumination request from the wine inventory hosted services computing system to the smart caps satisfying the first set of criteria, in at least one example. The smart caps may then receive the illumination request from the wine inventory hosted services computing system and control one or more lights of the smart cap in accordance with the illumination request. Such communication of the illumination request and subsequent illumination of the smart caps may be performed via any one or combination of the manners discussed herein. For example, in at least one embodiment, the illuminating module of the wine inventory hosted services computing system may send an illumination request to one or more smart caps via the communication subsystem of the wine inventory hosted services computing system, and the communication subsystem of corresponding one or more smart caps may receive the illumination request. Then, the illumination displaying module of the cap computing system of the one or more smart caps may illuminate one or more indicator lights via display subsystem of the cap computing system, where the cap computing system communicates with the one or more indicator lights of the smart cap, such as an LED board.

In some examples, following illumination of the smart caps for the first wine set at step 912, method 900 may further include receiving a second set of criteria at step 914. The second set of criteria may be received via a user input to the wine inventory management system via user input to the wine inventory application through a wine inventory device, for example. Any of the possibilities discussed above in regards to the manner in which the first set of criteria is received and the types of first criteria that may also apply to the second set of criteria.

After receiving the second set of criteria at step 914, it may be determined that one or more wines of a wine collection satisfies the second set of criteria to form a second wine set at step 916. For example, the one or more wines are determined to satisfy the second set of criteria to form the second wine set via the wine inventory hosted services. The second set of criteria may be based on a condition of the wines in some examples.

Further, in some embodiments, method 900 may include additionally illuminating smart caps for the second wine set at step 918. For example, the smart caps for the second wine set may be illuminated, and the smart caps for the first wine set may be dimmed compared to the smart caps illuminated for the second wine set. In another example, the smart caps for the first wine set and the second wine set may be illuminated in different colors or light animation patterns. Alternatively, the smart caps for the first wine set may be transitioned from being illuminated to being unilluminated upon receiving the second set of criteria at step 914, and the second wine set may be illuminated. It is noted that although only two sets of criteria are shown in method 900, in some examples, more or fewer than two sets of criteria may be possible. The smart caps for the second wine set may be illuminated in any one or combination of manners as discussed above.

Following step 918, the indicator lights of the smart caps of one or more of the first wine set and the second wine set may be turned off at step 920. For example, in cases where the smart caps of the first wine set were dimmed compared to the second wine set or illuminated in a different color, animation pattern, etc. than the second wine set at step 918, then method 900 may include turning off both the indicator lights of the first wine set and the second wine set at step 920. In other examples where only the second wine set is in an illuminated state at step 920, then only indicator lights of the smart caps of the second wine set may be turned off at step 920. Moreover, in some examples where the both the first wine set and the second wine set are in an illuminated state at step 920, it may be desirable to transition the second wine set back to the unilluminated state. Thus, the indicator lights of the smart caps of the second wine set may be turned off at step 920. In some examples the smart caps may be illuminated for a threshold amount of time and then the indicator lights of the smart caps may be turned off. Further, in at least one example, a user may indicate that the indicator lights of the smart caps may be turned off. For example, an input may be received from the user via the wine inventory application indicating that the smart caps of one or more of the first wine set and the second wine set no longer need to be illuminated.

The following include example wine searches that may be performed via a wine inventory application of an example wine inventory management system. In a first example wine search. The example, the wine inventory application may display a wine search screen. The wine search screen may include several categories. Categories for searching for a wine may include one or more of varietal, winery, region, food pairing, recently added, 90+ rated wines, and wines to drink now, in some examples. The recently added category may include wines recently added to a wine collection. The 90+ rated wines category may include top rated wines based on critics' ratings according to a hosted system of the wine inventory management system. The wines to drink now category may be based on a wine collection that may be in peak condition in some examples. In other examples, the wines to drink now category may additionally or alternatively be based on wines trending in a social network or wines that are designated as featured wines.

A category may be selected responsive to a user input received via the device operating the wine inventory application. Smart caps associated with the selected category may be illuminated in some examples. After a category is selected, the wine inventory application may display a sub-category screen. The sub-category screen may display a list of sub-categories related to the category already selected. For example, if varietals was the category selected, a list of different varietal may be the sub-categories listed.

A sub-category may then be selected from the sub-category list to search for wines only related to the selected sub-category. For example, a wine varietal may be selected from the list of sub-categories.

After selecting a sub-category from a list of sub-categories, the application may display a results screen. The results screen may display a list of wines that meet the sub-category criteria selected. For example, a list of wines that match the varietal that was selected may be displayed.

Additionally, smart caps that are associated with wines that satisfy the sub-category criteria may be illuminated. Smart caps that are not associated with wines that satisfy the sub-category criteria may be illuminated in a different manner than the smart caps that are associated with wines that satisfy the sub-category criteria.

For example, the smart caps that are not associated with wines that satisfy the sub-category criteria may be dimmed compared to the smart caps associated with wines that satisfy the sub-category criteria. In other examples, there may be different light animations, images, or colors for smart caps associated with wines that satisfy the set of sub-category criteria compared to the light animations of the smart caps associated with wines that do not satisfy the set of sub-category criteria. In still other examples, smart caps associated with wines that satisfy the set of sub-category criteria may be illuminated while the smart caps associated with wines that do not satisfy the set of sub-category criteria may not be illuminated.

In example wine searches where a set of criteria may be incrementally refined, smart caps associated with wines that satisfy different sets of criteria may be illuminated differently as the set of criteria for the search is refined. In one example, smart caps may be illuminated on a scale from no illumination to full illumination, where the more criteria a wine with which a smart cap is associated satisfies, the more that smart cap will be illuminated. For example, smart caps associated with wines that do not satisfy any of a set of criteria may not be illuminated, smart caps that are associated with wines that satisfy a portion of a set of criteria may be dimmed compared to smart caps that satisfy all of a set of criteria, and smart caps that are associated with wines that satisfy all of the set of criteria may be fully (i.e., brightly) illuminated. In other examples, different light animations, images, hues of a color, or different colors may be used.

In some examples, a user may then further refine the results by selecting a filter. A filter may be applied responsive to selection of a filter from a list of filters. The selected filter may be applied to the list of wines displayed after selecting a sub-category to further refine the list of wines, for example. The list of filters may include filters such as ready to drink, 90+ rating, special occasion, pricing, or wine characteristics filters, for example. A filter may be selected responsive to a user input. In some examples, a filter may be applied responsive to selection of an on/off toggle button displayed. After a filter is selected, the filter may be applied to the list of wines. However, in some examples, a user may not apply any filters to the wine list.

One or more wines may be selected from a list of wines following one or more of the above search steps. The wine may be selected from the list of wines before applying a filter in some examples. In other examples, a wine may be selected from a refined list of wines displayed after applying a filter to the list of wines. Smart caps that are associated with wines in the refined list may be illuminated. Smart caps that are associated with wines that do not meet the refined list of requirements may be illuminated in any of the ways described above.

After selection of a wine from either a refined or unrefined list of wines, a wine details screen may be displayed. In some examples, smart caps associated with the wine selected from either the refined or unrefined list of wines may be illuminated. The wine details screen may display details about the selected wine. In some examples, the details displayed may include information about the selected wine such as the wine's label, name, rating, price, categorization, drinkability, and tasting notes. The drinkability of the wine may be based on whether or not the wine is in peak condition, in some examples.

From the wine details screen displayed, a wine may be marked as a favorite, shared with other users, reviews of the selected wine may be displayed, and tags related to the selected wine may be displayed. Tags related to the selected wine may include tags such as the varietal, year, or region of the selected wine. The tags may be selected to view all wines that share the same tag. For example, if a pinot noir tag is selected from a wine details screen, another screen may be displayed with a list of wines that also have a pinot noir tag associated with them. Then, the example wine search may end.

In a second example wine search performed via the wine inventory application, a wine search screen may display a list of categories. A category may be selected from the list of categories. A category may be selected responsive to a user input, for example. The category selected may be a winery category.

Responsive to the winery category being selected, a list of wineries may be displayed. A winery may be selected from the list of wineries. For example, a winery may be selected from the list of wineries responsive to a user input. After selection of a winery from a list of wineries, a results screen may be displayed.

The results screen may display a list of wines 3216 associated with the winery 3214 selected at 3204. Smart caps associated with the wines may be illuminated, in some examples. In examples where the smart caps associated with wines are illuminated, any of the illumination strategies discussed in reference may be used.

A wine may be selected from the list of wines in some examples. If a wine is selected from the list of wines, then the wine inventory application may display a wine details screen. A wine may be selected from the list of wines responsive to a user input. Smart caps associated with the wine selected from the list of wines may be illuminated. In examples where the smart caps associated with the selected wines are illuminated, any of the illumination strategies discussed in reference to may be used.

In other examples, however, a wine may not be selected from the list of wines, and instead a filter may be applied to the list of wines. A filter button may be selected in order to display a filter screen. The filter screen may include a list of filters that may be applied to the list of wines. Filters may include price, wine characteristics, wine rating, whether a wine is ready to drink, or whether a wine is a special occasion wine, for example. A filter may be selected responsive to a user input. In some examples, selecting a filter may include selecting on on/off toggle button. After selecting the filters to be applied to the list of wines, an apply button may be selected to apply the selected filters to the wine list.

After the filters have been applied, a list of wines may be refined to only display wines that meet the criteria of the selected and applied filters. Smart caps associated with the refined wine list may be illuminated. In some examples, smart caps that were illuminated before the filter was applied may no longer be illuminated after the filter is applied if they do not meet the new search criteria. However, any of the illumination strategies discussed in reference to may be used.

A user may then select a wine from this refined list of wines. After selecting a wine from the refined list of wines, a wine details screen may be displayed. Additionally, smart caps associated with the wine selected from the refined list of wines may be illuminated. Any of the illumination strategies discussed above may be used.

Next, a wine details screen may display information about a selected wine. The information may include the selected wine's label, name, rating, price, categorization, drinkability, and tasting notes.

From the wine details screen displayed, a wine may be marked as a favorite, shared with other users, reviews of the selected wine may be displayed, and tags related to the selected wine may be displayed. Tags related to the selected wine may include tags such as the varietal, year, or region of the selected wine. The tags may be selected to view all wines that share the same tag. For example, if a pinot noir tag is selected from a wine details screen, another screen may be displayed with a list of wines that also have a pinot noir tag associated with them. Then, the example wine search may end.

A third example wine search that may be performed via the wine inventory application of the wine inventory management system is provided.

In the third example wine search, a wine search screen may display a list of categories. A category may be selected from the list of categories. A category may be selected responsive to a user input, for example. The category selected may be a region category.

After the region category is selected, a list of countries may be displayed. A country may be selected from the list of countries. For example, a country may be selected from the list of regions responsive to a user input. After selection of a country, a regions screen may be displayed. Smart caps associated with wines that are from the selected region may also be illuminated. Any of the illumination strategies discussed above may be used when illuminating the smart caps.

The regions screen displayed may display a list of regions that may be associated with the selected country. The regions may be an appellation from within the selected country. For example, if the country selected was the United States, a list of regions may be a list of states. Next, a region may be selected. In some examples, a region may be selected responsive to a user input.

After selection of a region, a sub-region screen may be displayed. In some examples, smart caps associated with wines that satisfy the region criteria selected may be illuminated. A list of sub-regions may then be listed. The sub-regions may be American Viticultural Areas (AVAs) in some examples. In other examples, the sub-regions may be viticultural areas designated by wine governing bodies for a selected country or appellate of a country. A sub-region may then be selected. The sub-region may be selected responsive to a user input in some examples.

After selection of a sub-region, a results list may be displayed. In some examples, smart caps associated with wines that satisfy the sub-region criteria selection may be illuminated. The results list may include a list of wines. A wine may be selected in some examples. After a wine is selected, a wine detail screen may be displayed. Smart caps associated with the wine selected may be illuminated. Any of the illumination strategies discussed above may be used.

In other examples, a filter button may be selected to apply a filter to the list of wines. After filter button is selected, a filter screen may be displayed.

The remainder of the steps of the flow chart corresponds to steps described above for the second example wine search regarding application of a filter.

In a fourth example wine search performed via the wine inventory application, a wine search screen may display a list of categories, and a food pairing category may be selected. In some examples, a food pairing category may be selected responsive to a user input. After selection of the food pairing category, a broad food category screen may be displayed.

The broad food category screen displayed may display a list of broad food categories. The broad food categories may include one or more of meat, seafood, pizza, pasta, dessert, and vegetarian, in some examples. A broad food category may be selected. For example, the meat broad food category may be selected.

Following selection of a broad food category, a food sub-category screen may be displayed. In some examples, smart caps associated with wines that pair well with the selected broad food category may be illuminated. Any of the illumination strategies discussed above may be used.

The food sub-category screen may display a list of food sub-categories that may be related to the selected broad food category. For example, following selection of the meat broad food category, a list of different types of meats may be the food sub-categories displayed.

A food sub-category may then be selected. In some examples where a list of different types of meats may be the food sub-categories, pork may be the food sub-category selected.

Following selection of a food sub-category, a food dish screen may be displayed. In some examples, smart caps associated with wines that pair well the selected food sub-category may also be illuminated. Any of the illumination strategies discussed above may be used.

The food dish screen may display a list of food dishes that correspond with the food sub-category selected. For example, if the food sub-category selected was pork, then the food dishes displayed may include food dishes that use pork (e.g., pork chops).

A food dish may then be selected from the food dishes displayed. Following selection of a food dish, a wine results screen may be displayed. In some examples, a recipe for the selected food dish may also be displayed. In some embodiments, smart caps associated with wines that pair well with the selected food dish may be illuminated. Any of the illumination strategies discussed above may be used. The wine results screen may display a list of wines that may be recommended to be paired with the food dish selected.

A wine may then be selected in some examples. After a wine is selected, a wine detail screen may be displayed. In some examples, smart caps associated with the selected wine may be illuminated. Any of the illumination strategies discussed above may be used.

In other examples, a filter button may be selected to apply a filter to the list of wines. After filter button is selected, a filter screen may be displayed.

The remainder of the steps may correspond to the other filtering steps described above in the other example wine searches. Following selection of a wine, the wine search may end.

Further, a fifth example wine search in the wine inventory application of the wine inventory management system is provided.

The fifth example wine search begins where a wine search screen may be displayed. The wine search screen may display a list of categories. A subset of categories may be direct to results categories. Direct to results categories may be categories that cause a wine results screen to be displayed responsive to selection. The categories that may not be direct to results categories may cause additional category selection screens to be displayed responsive to being selected.

The direct to results categories may include categories such as recently added, 90+ ratings wines, favorites, or wines to drink now, in some examples. Other direct to results categories may include an I'm Feeling Lucky category that may generate a random list of wines via a randomizing algorithm, a Test Flight category that may generate a list of wine flights, a Tastings category that generates a list of wines to taste during a wine tasting for a user to develop their wine sensory skills.

The direct to results categories may also include categories such as featured wines. Featured wines may be a list of wines recommended based on variables such as a time of day, day of the week, time of the year, or special occasion. For example, the wine inventory application may have access to a user's calendar, and if it is determined that it is special occasion for a user (e.g., an anniversary) a wine may be recommended in a direct results category for the user. In other examples, wines on a Featured wines list may be based a list of sponsored wines, expert picks by a sommelier, wines that are popular in a social media network, or wines that are frequently purchased according to information stored at hosted services of the wine inventory management system. While these are some example direct to results categories, other categories may be possible.

A user may select a direct to results category in the fifth example wine search. Responsive to selection of a direct to results category, a wine results screen may immediately be displayed. The wine results screen may display a list of wines that corresponds with the direct to results category selected. In some examples, smart caps associated with wines in the selected direct to results category may be illuminated. Any of the illumination strategies discussed in reference may be used.

In one embodiment, a wine may then be selected. After a wine is selected, a wine detail screen may be displayed. Smart caps associated with the wine selected may be illuminated in some examples. Any of the illumination strategies discussed above may be used.

In other embodiments, a filter button may be selected to apply a filter to the list of wines. After filter button is selected, a filter screen may be displayed.

The remainder of the steps of the flow chart corresponds to similar filtering steps as described above in regards to the other example wine searches.

The wine inventory application of the wine inventory management system may include a home screen. In some examples, home screen may display a find a wine button. The find a wine button may be selected in order to initiate a wine search, such as one of the example wine searches described above. The find a wine button may be selected responsive to a user input. In some examples the user input may be tapping the find a wine button.

The wine inventory application of the wine inventory management system may include a wine search screen of the wine inventory application. The wine search screen may include categories for a wine search. A first subset of categories may be direct to results categories. Direct to results categories may cause the wine inventory application to display a results screen responsive to being selected. The results screen may display a list of wines. Examples of direct to results categories may include recently added, 90+ rated wines, or wines to drink now categories. Other direct to results categories may be possible. In some examples, a wine search screen may not have any direct to results categories.

A second subset of categories may be nested search categories. Nested search categories may be categories that cause the wine inventory application to display a screen with another list of categories for a wine search responsive to being selected. Nested search categories may not cause the wine inventory application to display a results screen with a list of wines responsive to being selected. Some example nested search categories may include varietal, winery, region, or food pairing. Other nested search categories may be possible. In some examples, a wine search screen may not include any nested search categories.

The wine search screen may also include a navigation button. The navigation button may include the title of the screen that is currently being viewed and a directional arrow. In some examples, the directional arrow may cause the wine inventory application to display a previously displayed screen responsive to being selected. For example, if wine search screen was displayed responsive to selection of a find a wine button on home screen, a user may select the directional arrow of navigation button from wine search screen to be returned to home screen.

Wine search screen may also include a menu button. In some examples, the menu button may cause the wine inventory application to display a menu that includes one or more of navigational buttons and action buttons.

The wine inventory management system may include a sub-category screen. The sub-category screen may be displayed responsive to selection of a category. The sub-category screen may include a list of sub-categories. The sub-categories listed on sub-category screen may be sub-categories of a selected wine search category. For example, the sub-categories displayed on screen may be different varietals if a varietal wine search category has been selected. The sub-category screen may also include a navigational button and menu button similar to wine search screen.

The wine inventory application of the wine inventory management system may include a results screen. The results screen may display a list of wines. In some examples, the results screen may be displayed responsive to the selection of a wine search category. The list of wines may be listed by one or more of wine name, year, varietal, number of bottles available, and a volume of each wine bottle.

The wine inventory application of the wine inventory management system may include a filter screen in some examples. The filter screen may be displayed in order to refine a list of wines of a results screen. The filter screen may display filters that may be applied to a list of wines displayed on a wine results screen. In some examples, the filters may include one or of filters for a wine color (e.g., red, white, or rose), filters for a wine characteristic (e.g., ready to drink now, rating 90+, or special occasion), or filters for a price of the wine. One or more filters may be selected responsive to a user input. In some examples, one or more filters may be selected responsive selection of one or more buttons. The buttons may be on/off toggle buttons, check boxes, or highlighting buttons. Other buttons may be possible, however.

The wine inventory application of the wine inventory management system may include a wine details screen. The wine details screen may be displayed responsive to selection of a wine from a results screen in some examples. The wine details screen may display information about a wine. The information about the wine may be displayed near a photo of a bottle of the wine. In some examples, however, a photo of a bottle of the wine may not be included.

Information displayed about the wine may include listed information and summarized information. Listed information about the wine may include one or more of a year the wine was produced, a name of the wine, the country in which the wine was produced, the volume of a bottle of the wine, and an alcohol by volume percentage listing. Listed information may be edited by a user in some examples.

Summarized information may include information that may be of immediate interest when selecting a wine. In some examples, this information may include a condition of the wine (e.g., peak condition, declining condition, etc.), a number of bottles of this wine that may be in the wine collection, and a price rating. The price rating may be represented in summarized information by a symbol (e.g., a dollar sign, two dollar signs, etc.) corresponding with a price range within which the wine falls, for example. In other examples, other information may be included in summarized information.

Additionally or alternatively, the wine details screen may display a wine rating and description of the wine. For example, the wine rating and description of the wine may be a review of the wine by a wine critic. Wine details screen may also include tasting notes for the wine. The tasting notes may describe the aromas, tastes, or mouthfeel associated with the wine.

The wine detail screens may be accessible by a user via the wine inventory application of the wine inventory management system. Wine detail screens may display information about a wine. The information populating the wine detail screens in the wine inventory application may be from a wine database.

A first example wine detail screen may include an editing button for a user to edit information on the wine detail screen that may be incorrect. For example, after adding a wine to a wine collection, wine detail screen may be shown. If the information on the wine detail display is incorrect, a button for editing the information may be provided. The user may then edit the information in the wine detail screen to correct any errors. For example, if a user adds a new wine to a wine collection by taking a photo of the wine bottle or wine label, and the wine database matches that photo with the same wine that was produced in a different year, then the user may select the edit button and edit the year in the wine details screen to display the correct year.

In at least one example, the wine detail screen may provide a button for a user to indicate that they have drunk the wine described in the wine detail screen. Additionally or alternatively, the wine detail screen may provide a rating button for a user to indicate a rating of a wine. In some examples, the rating button may be displayed in the wine detail display after a user has indicated that they have drunk a wine. In some examples, the rating button may enable a user to rate a wine on a rating scale. In other examples, the rating button may enable a user to create a comment for the wine they may be rating on the wine detail screen.

In some examples, the wine detail screen may provide a favorite button and a rating. In some examples, the rating may be an average rating based on all users who have rated the wine in the wine details screen. In other examples, the rating may be the rating that the user provided for the wine detail screen. A favorite button may be selected by a user in the wine details screen to indicate that a wine of the wine detail screen is a favorite wine of the user, in at least one example. The indications of wine ratings and favorite wines provided by the user may be used by hosted services to make wine recommendations, in some examples. In other examples, the indications of wine ratings and favorite wine provided by the user may be user to organize wines in the wine inventory application of the wine inventory management system.

Additionally or alternatively to the description provided above, the wine inventory application of the wine inventory management system home screen may display a menu comprising a plurality of sections. The sections may be different sizes. For example, a first section may be larger than a second section. However, in some examples the sections may all be the same size.

Each section of home screen may display a button. These buttons displayed in each section may be selected in order to navigate to another screen of the wine inventory application. In some examples, these buttons may be categories for beginning a wine search. For example, a home screen may display one or more of a winery button, a food pairing button, a special occasion wines, a wines to drink now button, a varietal button, a region button, a recently added button, and a 90+ rated wines button. Following selection of one of the buttons a wine search may be initiated.

Further, though many of the above examples relate to illuminating smart caps responsive to receiving a user input via a wine inventory application, the smart caps may also be illuminated due to receiving a user input at the physical smart cap itself.

For example, a battery checking sequence may be initiated responsive to a smart cap receiving a user input.

User input for initiating a battery checking sequence may include pressing button of the smart cap. For example, a battery checking sequence may be initiated responsive to a button of the smart cap being double pressed. Double pressing the button may include pressing and releasing button two times within a threshold timeframe. For example, double pressing the button may include pressing and releasing the button two times within two seconds.

Following initiation of a battery checking sequence, indicator lights of the smart cap may be illuminated. In some examples, a color that indicator lights are illuminated responsive to initiation of a battery checking sequence may correspond to a state of charge (SOC) of a battery of the smart cap. For example, indicator lights may be illuminated in green responsive to a battery SOC being greater than a first threshold, illuminated in yellow responsive to a battery SOC being less than the first threshold and greater than a second threshold, and illuminated in red responsive to a battery SOC being less than the second threshold. In one example, the first threshold may be a battery SOC greater than 80%, the second threshold may be a battery SOC greater than 20%, and the third threshold may be a battery SOC less than 20%.

Following the illumination of indicator lights, the battery checking sequence may end. In some examples, the battery checking sequence may end after indicator lights have been illuminated for greater than a threshold amount of time.

Though the battery SOC of a smart cap may checked responsive to a manual input to the smart cap itself, it is also possible in at least one embodiment to check the SOC of one or more smart caps responsive to a user input to the wine inventory application. For example, a low battery warning display may be initiated to indicate the smart caps of a smart cap display that have batteries with a state of charge (SOC) less than a threshold state of charge responsive to a user input to the wine inventory application. In some examples, a low battery warning display may be initiated responsive to exceeding a threshold period of time since a last low battery warning display was initiated. For example, a low battery warning display may be initiated responsive to exceeding one month since the last low battery warning display was initiated.

Following initiation of a low battery warning display, smart caps that have batteries with less than a threshold SOC may be illuminated. Smart caps that have a battery SOC greater than the threshold SOC following initiation of the low battery warning display may not be illuminated.

After determining which smart caps of smart cap display have battery states of charge greater than the threshold and less than the threshold, a notification may be sent to a wine inventory application of the wine management system. This may enable a user to identify wine bottles with smart caps that need to be recharged or that have batteries that may need to be replaced.

Turning back now to operations that may be carried out via a manual user input, in another example included receiving a user input at the smart cap itself, a wine checking sequence may be initiated responsive to a user input, the user input being pressing of a button of the smart cap. For example, the user input may include a button of the smart cap being pressed and released in less than a threshold amount of time. In some examples, the threshold amount of time may be two seconds.

Responsive to the smart cap receiving the user input, a wine checking sequence may be initiated. The wine checking sequence may include the smart cap communicating with hosted services via a gateway system to determine a condition of the wine associated with the smart cap. For example, an output indicating the condition of a wine from hosted services may be communicated to the smart cap via a gateway system, and the smart cap may illuminate indicator lights in accordance with the output from the hosted services.

In some examples, the indicator lights of the smart cap may be illuminated in a color that corresponds with a condition of the wine associated with the smart cap. Indicator lights may be illuminated in a first color if the wine needs to be held for greater than a first threshold period of time before the wine is in peak condition. For example, if a wine needs to be held for greater than the first threshold period of time to be in peak condition, then indicator lights may be illuminated in red. Indicator lights may be illuminated in a second color if the wine needs to be held for less than the first threshold period of time before the wine is in peak condition. For example, if the wine needs to be held for less than the first threshold period of time before the wine is in peak condition, then indicator lights may be illuminated in purple. If a wine is in peak condition for drinking, then indicator lights may be illuminated in a third color. For example, if the wine is in peak condition, then indicator lights may be illuminated in green. Indicator lights may be illuminated in a fourth color if the wine has been past a peak condition for less than a second threshold period of time. For example, if the wine has been past a peak condition for less than the second threshold period of time, then indicator lights may be illuminated in yellow. Indicator lights may be illuminated in a fifth color if the wine has been past a peak condition for greater than the second threshold. For example, if the wine has been past a peak condition for greater than the second threshold, then indicator lights may be illuminated in blue. Wine that has been past a peak condition for greater than the second threshold may have declined in quality, in some examples.

Following illuminating the indicator lights, the wine checking sequence may end. In some examples, the wine checking sequence may end following illuminating indicator lights for greater than a threshold period of time.

In another example, a data transferring sequence may be initiated responsive to a first user input t of pressing a button of a first smart cap, and a second user input of pressing a button of a second smart cap. In particular, the first input may include pressing and holding the button of the first smart cap for more than a threshold period of time. In some examples, the threshold period of time for holding the button of the first smart cap may be two seconds. Indicator lights of the first smart cap may be illuminated responsive to user input. In some examples, indicator lights may be illuminated a particular color responsive to the user input. In other examples, the indicator lights may be illuminated with a particular light animation pattern responsive to the user input.

The second user input may include pressing the button of the second smart for more than a threshold period of time. In some examples, the threshold period of time for holding the button of the second smart cap may be two seconds. Indicator lights of the second smart cap may be illuminated responsive to user input. In some examples, indicator lights may be illuminated a particular color responsive to the user input to indicate that the data transferring sequence has been successfully initiated. In other examples, the indicator lights of the second smart cap may be illuminated with a particular light animation pattern responsive to the second user input to indicate that the data transferring sequence has been successfully initiated.

Responsive to both the first user input and the second user input, a data transferring sequence may be initiated. Following initiation of the data transferring sequence, information associated with the first smart cap may become associated with the second smart cap. In some examples, information that may have been associated with the first smart cap may become associated with the second smart cap by communicating with hosted services via a gateway system to reassign the information associated with the first smart cap to the second smart cap. Such association may include communication with the wine inventory hosted services wine portfolio management sub-module.

If information originally associated with the first smart cap fails to become associated with the second smart cap, then the data transferring sequence may end. Indicator lights of the first and the second smart caps may be illuminated a particular color or with a particular light animation pattern to indicate failure of the data transferring sequence. The indicator lights of the first and the second smart caps may be turned off following illumination to indicate failure of the data transferring sequence.

If the information associated with the first smart cap is successfully reassigned to become associated with the second smart cap, the data transferring sequence may end. Indicator lights of the first and the second smart caps may be illuminated a particular color or with a particular light animation pattern to indicate a successful data transferring sequence. Indicator lights of the first and the second smart caps may be turned off after indicating a successful completion of the data transferring sequence.

Figure 10:
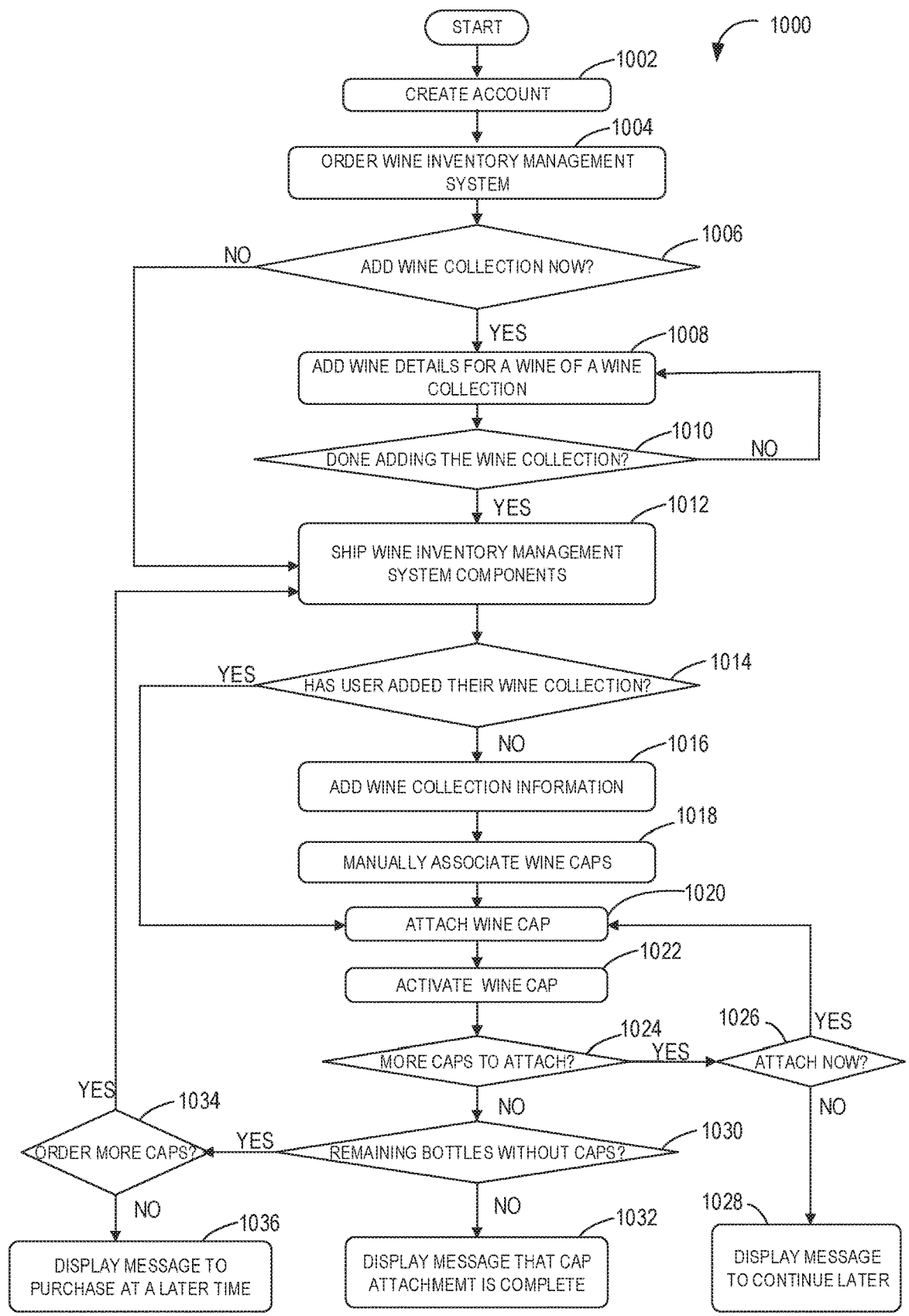
FIG. 10 shows an example flow chart of a second example method according to at least one embodiment of the present disclosure.

Turning now to FIG. 10, FIG. 10 shows a flow chart of a second example method 1000, according to at least one embodiment of the present disclosure. Method 1000 is an onboarding method for the wine inventory management system.

Onboarding method 1000 may begin at step 1002 where an account may be created. In at least one example, the account created may be a user account of the wine inventory management system. The user account may be created via an online portal on a wine inventory website that may connect to the wine inventory management system. The user account that is created may enable a user to manage a wine collection via the wine inventory management system. The website of the wine inventory management system may enable access to receive product recommendations, update information associated with the wine inventory management system (e.g., a wine inventory database), and to purchase products (e.g., smart caps, hubs, or wine). Upon creation of a user account on the wine inventory website of the wine inventory management system, a user may receive an email confirmation to an email address associated with the user account that is created.

Following creation of the user account, a web portal may be accessed to enter basic information to be associated with the user account. For example, the user account may be accessed on the wine inventory website to enter basic information such as the name, age, email address, etc. Additionally, in at least one example, the user account may be created and user information may added via the wine inventory application of the wine inventory management system.

Following the creation of a user account, and, in at least one example, the addition of basic information at step 1002, onboarding method 1000 may include ordering the wine inventory management system responsive to a user input at step 1004. For example, at step 1004, a user input may be received to order the wine inventory management system, where ordering the wine inventory management system may include ordering at least one hub and at least one smart cap. Further, ordering the wine inventory management system may include downloading the wine inventory application responsive to receiving a user input in at least one example.

Following ordering the wine inventory management system at step 1004, step 1006 of the onboarding method 1000 may include differentiating between whether a wine collection is to be added now or whether a wine collection is to be added later. For example, at step 1006, following ordering the wine inventory management system at step 1004, a display may be provided prompting a user to confirm whether or not the user is going to add a wine collection to be associated with the wine inventory management system that was ordered at step 1004.

Responsive to determining that the wine collection is to be added now, which may be determined responsive to receiving a user input to the above prompt in at least one example, onboarding method 1000 may include adding wine details for a wine of a wine collection at step 1008.

For example, in at least one embodiment, wine details may be semi-automatically received by receiving an image of a wine bottle label for a wine of a wine collection at the wine inventory application and then utilizing optical character recognition to add that wine and corresponding wine details that may be associated with that wine in a wine database to the wine collection. For example, a camera of the device running the wine inventory application may be accessed to receive the image of the wine bottle label. Alternatively, images that are already saved on a device running the wine inventory application or wine inventory website may be uploaded to the wine inventory application or to the wine inventory website to add details for a wine of a wine collection via OCR.

For examples where a photo of a wine label is received for semi-automatically adding wine details for a wine of a wine collection, a wine inventory application of the wine inventory management system supported by hosted services may utilize optical character recognition (OCR) to search for the wine based on information detected from the wine label.

Next, if a wine matching a wine search is found, the match may be confirmed as being correct responsive to a user input. For example, a user input to a wine inventory application of the wine inventory management system may confirm the correct wine has been found.

Following confirmation that a correct wine has been found, that wine and the corresponding wine details may be added to a wine collection. In some examples, the wine may be added to a digital wine collection that is managed via the wine inventory application of the wine inventory management system. Wine details that may be associated with the wine that has been added to the wine collection may be accessible for viewing via the wine inventory application of the wine inventory management system or via the wine inventory website.

If a match is not found following receiving an image of a wine label, then a no match screen of the wine inventory application may be displayed. In some examples, the picture of the wine bottle label that could not be matched in the wine database may be sent to experts supporting the wine inventory management system. The experts supporting the wine inventory management system may then identify the wine that did not have a match and add the wine that did not have a match to the wine database. A smart cap with which a user was trying to pair the bottle of wine may be automatically updated after the wine that did not have a match is added to the wine database. In the meantime, however, a user may manually enter the wine details for the wine that did not have a match in the wine database.

Additionally or alternatively, wine details for a wine of a wine collection may be manually added via a user input. Manually inputting wine details at step 1008 may include performing a search in a wine database that is accessible via the wine inventory website or the wine inventory application. When adding wine details, one or more of a winery, a wine type, a year, and an amount of bottles of the particular wine being added to the wine collection may be indicated.

For example, a user may manually input wine details for a wine of a wine collection. Any one or combination of the criteria discussed above for performing a wine search may be involved in performing a search in the wine database of the wine inventory management system. For example, one or more of a vintage, and other metadata may be input by a user to find a wine of a wine collection that is to be added. It is noted that the wine details for the wine of the wine collection received at step 1008 may be stored in the wine inventory database of the wine inventory hosted services. In at least one example, a wine may need to be manually added to the wine collection of a user due to the wine not being available in the wine database of the wine inventory management system. Thus, in such examples where a wine in a wine collection may not be available in the wine database and, as such, is manually added, the wine database may be updated with the new wine manually added by the user in at least one example.

After receiving wine details for a wine of a wine collection at step 1008, step 1010 may include differentiating between whether a user is done adding the wine collection and whether the user is not done adding the wine collection. For example, step 1010 may include prompting a user to indicate whether the user is done adding the wine collection or whether the user is not done adding the wine collection.

Method 1000 may include determining that the user is not done adding the wine collection responsive to receiving a user input at step 1010. Responsive to determining that the user is not done adding the wine collection at step 1010, method 1000 may include repeating steps 1008 and 1010 until it is determined at step 1010 that the user is done adding the wine collection.

Responsive to determining that the user is done adding the wine collection responsive to receiving a user input at step 1010, method 100 may include shipping the wine inventory management system to the address associated with the user account at step 1012. Further, responsive to determining that the user is done adding the wine collection at step 1010, method 1000 may include providing a dashboard display including one or more of tracking information, a checklist of items that need to be complete (account set up, adding a wine collection, attaching smart caps, etc), user account information, settings, marketing modules from wineries, links to download the wine inventory application.

The wine inventory management system, including the smart cap(s) and hub(s) that are shipped at step 1012, may be synced with the wine details received at step 1008 prior to shipment. Thus, in examples where a user may add the wine collection at steps 1008 and 1010, as opposed to opting to add the wine collection later, the wine inventory management system may be shipped with smart caps pre-associated with a wine of the wine collection. For example, if enough smart caps are ordered to accommodate each wine added at step 1008, then a smart cap may be sent pre-associated each wine added at step 1008. In cases where an insufficient number of smart caps are ordered to accommodate all of the wines in a wine collection, a user may be notified that more smart caps need to be ordered to accommodate all of the wines of the wine collection. Additionally or alternatively, only some of the wines of the wine collection may have a pre-associated smart cap. Alternatively, in examples where more smart caps are ordered than wines in the wine collection, and thus more smart caps are shipped to a user than there are wines in the wine collection, only some of the smart caps may be pre-associated with the wines of the wine collection, and the remaining extra smart caps may be associated at a later time.

It is noted that in a case where it is determined at step 1006 responsive to a user input that the wine collection was to be added at a later time, method 1000 may have moved from step 1006 to step 1012 without involving steps 1008 and 1010. Thus, in such cases, the wine inventory management system that is shipped at 1012 may be shipped without any of the smart caps pre-associated with the wines of a wine collection of the user.

Following shipping the wine inventory management system at step 1012, onboarding method 1000 may include additional set-up steps from steps 1014-1034. In at least one example, the additional set-up steps from 1014-1034 may be performed carried out via one or more of the wine inventory application or wine inventory website, the smart caps, and the hub. For example, a user may log into the wine inventory application or the wine inventory website and be prompted to set-up the wine inventory system.

Starting at set-up step 1014, it may be determined whether a user has already added their wine collection. For example, a user may log-in to their account (e.g., via the wine inventory website or via the wine inventory application). Then, based upon whether wine details were added at step 1008 or whether a wine collection was opted to be added at a later time, it may be determined whether the user has already added their wine collection.

In examples where it is determined that the wine collection has not already been added at step 1014, method 1000 may include adding wine collection information at step 1016. For example, after determining that the wine collection has not already been added at step 1014, method 1000 may include displaying a message prompting a user to input wine collection information.

Then, at step 1016, wine collection information may be added responsive to a user input. For example, the step of receiving wine collection information at step 1016 may be substantially similar to the step of receiving wine details for a wine of a wine collection described at steps 1008 and 1010. Thus, the wine collection information received may be received in a semi-automated manner or via manual input.

A pairing sequence to manually associate each of the one or more wines that was added at step 1016 with a smart cap may then be initiated at step 1018. For example, the pairing sequence to manually associate the wine that was added at 1016 may be initiated responsive to a user input to the wine inventory application of the wine inventory management system to select one of the wines added at 1016 to be associated with a smart cap. Additionally, initiation of the pairing sequence to manually associate the wine that was selected with a smart cap may include one or more smart caps that are to be associated with the selected wine receiving a user input.

Following initiation of the pairing sequence, a hub system may prepare to assign the one or more smart caps that received the user input to the wine selected. Examples where more than one smart cap may be paired with the selected wine may be advantageous for efficiently assigning multiple bottles of the same wine to multiple smart caps. For example, assigning smart caps to wine bottles of a case of the same wine may be accomplished more efficiently. In some examples, a hub system may go into a discoverable mode, so that communication between one or more smart caps and the hub system may be established.

Following the user input to the one or more smart caps, a pairing to associate the wine with the one or more smart cap may be attempted. An indication may then be provided to indicate whether or not a pairing was successful.

For example, if a pairing was successful, indicator lights of the smart cap that is being paired may be illuminated in a first color. If the pairing was unsuccessful, the indicator lights of the smart cap that is being paired may be illuminated in a second color. For example, a successful pairing may be indicated by illuminating the indicator lights of the smart cap being paired in green, and an unsuccessful pairing may be indicated by illuminating the indicator lights of the smart cap being paired in red.

Additionally, an output to a wine inventory device operating the wine inventory application of the wine inventory management system may indicate whether or not the pairing was successful. If pairing was unsuccessful, the method may include attempting to pair the wine and the smart cap again.

If pairing was successful, the method may include displaying a prompt add another of the same bottle or to confirm that all of the smart caps that needed to be paired to the selected wine added are successfully paired. If more smart caps need to be paired with the selected wine following a successful pairing, the method may include not confirming that all of the smart caps that needed to be paired are paired, and the pairing sequence may be repeated to pair another smart cap with the selected wine. If all of the smart caps that needed to be paired to the selected wine added are successfully paired, then it may be confirmed that all of the smart caps that needed to be paired have been paired. Then, the above pairing process may be repeated for each wine that was received at step 1016. Following confirmation that all of the smart caps have been paired to the wine added, the hub system may exit discoverable mode.

In examples where it is determined that the wine collection has already been added, following step 1014, method 1000 may include attaching a smart cap (i.e., cap) to a wine of the wine collection at step 1020. For example, to attach a smart cap at step 1020, a user may open the wine inventory application of log into their account on the wine inventory website, and provide an input to begin cap attachment. Responsive to the wine inventory application/website receiving a user input to begin smart cap attachment, a wine of the wine collection that was already inputted at step 1008 may be displayed and the user attaches a smart cap to the bottle of wine that is displayed.

Then, following attaching the smart cap to the bottle of wine displayed via the wine inventory application or the wine inventory website at step 1020, method 1000 includes turning on the smart cap at step 1022 to activate the smart cap, and the smart cap may communicate back to the wine inventory application/website. The smart cap may be turned on responsive to a user input to the smart cap that was attached at step 1020, for example.

After the smart cap is turned on, during activation the smart cap may communicate with the wine inventory application/website via wine inventory hosted services due to communication between the smart cap and the hub. In at least one example, however, the smart cap may communicate with the device operating the wine inventory application via Bluetooth, through the hub, or through another wireless connection without first being channeled through the wine inventory hosted services. It is noted that if activation of the smart cap at step 1022 is unsuccessful (i.e., the attached smart cap does not communicate with the wine inventory management system), then an error message may be displayed with troubleshooting directions.

Otherwise, if the activation of the smart cap is successful at step 1022, the step 1024 may include displaying a message prompting a user to indicate whether or not there are more smart caps to attach to wines of the wine collection. Responsive to a user input, it may be differentiated between whether there are more smart caps to attach or whether there no more smart caps to attach at step 1024.

If it is determined that there are more smart caps to attach at step 1024, then method 1000 may include displaying a message at 1026 prompting a user to indicate whether or not the smart caps that still need to be attached are going to be attached now. Responsive to a user input, it may be differentiated between whether the smart caps that have not yet been attached are to be attached now or are to be attached at a later time.

Responsive to determining that the smart caps that have not yet been attached are to be attached now at step 1026, method 1000 includes moving to step 1020 to attach another smart cap and repeat the steps of 1020 to 1024.

Responsive to determining that the smart caps that have not yet been attached are to be attached at a later time at step 1026, method 1000 includes displaying a message that there are still smart caps that need to be attached and that the smart caps that still need to be attached may be attached at a later time.

Moving back to step 1024, if it is determined that there are no more smart caps to attach to wine bottles responsive to a user input at step 1024, then method 1000 may include differentiating between whether there are remaining wine bottles of the wine collection that do not have a smart cap. For example, a message may be displayed prompting a user to provide an input indicating whether there are remaining wine bottles without caps at step 1030 or whether there are no more wine bottles without smart caps at step 1030.

Responsive to determining that there are no more remaining wine bottles without smart caps at step 1030, method 1000 may displaying a message indicating that the smart cap attachment for the wine collection is complete at step 1032. The message may be displayed via the device running the wine inventory application or the device on which the wine inventory website has been accessed, for example.

Responsive to determining that there are remaining wine bottles without smart caps at step 1030, method 1000 may include displaying a message at step 1034 requesting a user input to differentiate between whether to order more smart caps or whether not to order more smart caps. For example, a message requesting a user to confirm whether or not to order more smart caps may be displayed via the device running the wine inventory application or the device on which the wine inventory website has been accessed.

Responsive to determining that more smart caps are to be ordered at step 1034, method 1000 may proceed back to step 1012 to ship more smart caps. For example, responsive to determining that more smart caps are to be ordered at step 1034, then order details, such as a number of smart caps, may also be received via a user input. Thus, the step of shipping wine inventory management system components at step 1012 may include shipping components according to order information collected via user input at step 1034.

Responsive to determining that no more smart caps are to be ordered at step 1034, method 1000 may proceed to step 1036 where a message may be displayed to convey to the user that additional smart caps may be ordered at a later time. For example, the message at step 1036 may be displayed via the device operating the wine inventory application or the device on which the wine inventory website is accessed.

Turning now to FIGS. 11A to 11C, FIGS. 11A to 11C show multiple views of another example smart cap according to at least one embodiment of the present disclosure. The example smart cap may include any one or combination of the features described above for the smart caps of the wine inventory management system.

Turning first to FIG. 11A, FIG. 11A shows a side view 1102 of the example smart cap. Similar to the other smart described herein, the example smart cap may include an indicator portion 626 and a mounting portion 624. The indicator portion 626 may be substantially similar to that of the other indicator portions 626 described herein. The indicator portion 626 may twist into the mounting portion 624 of the smart cap to couple the indicator portion 626 and the mounting portion 624, in at least one example. As such, the indicator portion 626 may be detachable from the mounting portion 624 of the example smart cap. Such the ability to detach the indicator portion 626 from the mounting portion 624 of the smart cap may be beneficial to quickly replace indicator portions that may have microprocessors that are malfunctioning or indicator portions that may have a low battery state of charge, for example. In at least one example, the mounting portion 624 of the smart cap may comprise an outer housing 1108, where the outer housing 1108 includes threads on an inner surface of the outer housing 1108. The threads on the inner surface of the outer housing 1108 may mate with corresponding threads of the indicator portion 626 to couple the indicator portion 626 to the mounting portion 624. Other mechanisms for coupling the indicator portion 626 and the mounting portion 624 may also be possible, however. As shown in the side view 1102 of the example smart cap, indicator lights 112 may be visible from the side view of the example smart cap. It is noted that the indicator lights 112 may be in a ring formation around an outer surface of an indicator portion housing 1110. Such a ring formation of the indicator lights around the outer surface of the indicator portion housing 1110 may be advantageous to enable easy location of a wine bottle in a wine collection, for example.

Turning to FIG. 11B, FIG. 11B shows a top view 1104 of the example smart cap. As shown in the top view 1104 of the example smart cap, the indicator portion 626 of the example smart cap may also include indicator lights 112 in a ring formation in the top surface of the indicator portion. In particular, top surface of an indicator portion housing 1110 may comprise indicator lights 112 in a ring formation formed therein. Additionally, the top surface of the indicator portion 626 comprises a button 1112. As discussed above, button 1112 may be configured to receive a user input, in at least one example.

Turning now to FIG. 11C, FIG. 11C shows a bottom view 1106 of the example smart cap. The mounting portion 624 of the example smart cap, as shown in bottom view 1106, may be different than the previous mounting portions. In particular, the mounting portion 624 of the example smart cap may comprise a rigid body, and the mounting portion 624 of the example smart cap may simply be pushed over a cap, and in some cases, a neck portion of a wine bottle. For example, the mounting portion of the example smart cap may comprise a mounting ring 1116, where the mounting ring may be biased inwards towards a center of the example smart cap. When positioning the example smart cap on a wine bottle, the cap portion of the wine bottle may be received in wine cap receiving space 1114. As the cap portion of the wine bottle is received in the wine cap receiving space 1114, the mounting ring 1116 may be deformed in an outward direction. However, as the mounting ring 1116 is biased in an inward direction, the mounting ring 1116 may push over the cap of the wine bottle (and in some cases, a portion of the neck of the wine bottle) to couple the example smart cap to the wine bottle.

In some examples, though not shown, the mounting ring 1116 may comprise a plurality of thin projections For example the mounting ring 1116 comprising the projections may be housed within the outer housing, and the projections 1108 may be pushed over a top of a cap of a wine bottle in at least one example to couple the example smart cap to the wine bottle. The projections may then hold the smart cap on the wine bottle, as the projections may be biased inward, causing the projections to squeeze the bottle.

Turning now to FIGS. 12A-12D, FIGS. 12A-12D shows multiple views of another example smart cap according to at least one embodiment of the present disclosure.

Turning to FIG. 12A, FIG. 12A shows a front view of the example smart cap. The example smart cap may comprise an indicator portion 626 including one or more of the features of the other indicator portions discussed herein. Regarding the mounting portion 624, the mounting portion 624 of the example smart cap comprises one or more C-shaped clips 1208, similar to the C-shaped clip 1202 of the smart cap shown at FIG. 6. However, the one or more C-shaped clips 1208 may be oriented such that the one or more C-shaped clips 1208 are substantially concentric with an indicator portion 626 of the smart cap, and such that the C-shaped clips 1208 are substantially concentric with a cap and neck of a wine bottle upon mounting the example smart cap to a wine bottle. It is noted that although the example smart cap comprises one C-shaped clip, examples where there may be more than one C-shaped clips 1208 may provide a more stable coupling of the smart cap 110 to a wine bottle. The C-shaped clip 1208 comprises outwardly angled projections 1220a, 1220b to assist with positioning the C-shaped clip 1208 over the cap or neck of a wine bottle. For example, the outwardly angled projections 1220a, 1220b may assist in deforming the C-shaped clip 1208 in an outward direction when coupling the C-shaped clip 1208 to a cap or neck of a wine bottle.

Moreover as shown in the front view of the example smart cap at FIG. 12A, the indicator portion 626 may be coupled to an indicator receiving portion 1216 of the mounting portion 624 of the example smart cap. For example, the indicator portion 626 may be coupled to the indicator receiving portion 1216 of the example smart cap via mating threads. However, other coupling means may be possible. For example, a magnetic connection may couple the indicator portion 626 to the indicator receiving portion 1216 of the example smart cap. The indicator portion 626 may be detachable in at least one example. Additionally, the indicator portion 626 may comprise indicator lights 112 in a ring formation on an outer surface of the indicator portion 626, thus enabling the indicator lights 112 to be viewable from a side, front, or back of the example smart cap.

A bracket 1210 may couple the C-shaped clip 1208 to the indicator receiving portion 1216. Thus, the C-shaped clip 1208 may be mounted to the neck of a wine bottle, while the indicator 626 and the indicator receiving portion 1216 of the example smart cap may be positioned above a top surface of a cap of a wine bottle.

Regarding FIG. 12B, FIG. 12B shows a side view of the example smart cap. It is noted that FIG. 12B shows the same elements as discussed in FIG. 12A, from a different point of view. Thus, FIG. 12B will not be described further.

Turning to FIG. 12C, FIG. 12C shows a top view of the example smart cap. As shown in the top view of the example smart cap, indicator lights 112 may be in a ring formation on a top surface of the indicator portion 626 of the example smart cap. Such a configuration may be beneficial so that the indicator lights of the example smart cap may be viewable from more perspectives. For example, the indicator lights of the example smart cap may be viewable when the example smart cap is coupled to a wine bottle in a wine rack.

Turning now to FIG. 12D, FIG. 12D shows a bottom view of the example smart cap. As shown in FIG. 12D, the C-shaped clip 1208 comprises an open end 1212 and a closed end 1214 opposite the open end 1212. The C-shaped clip 1208 may comprise a rigid material that may be temporarily deformed to widen an open end 1212 of the C-shaped clip 1208, to enable coupling of the C-shaped clip 1208 to a neck and/or cap of a wine bottle. As shown in FIG. 12D, the bracket 1210 is coupled to the closed end 1214 of the C-shaped clip. 1208, coupling the C-shaped clip 1208 to the indicator receiving portion 1216. It is noted that in examples where there may be more than one C-shaped clip 1208, the bracket 1210 may couple the multiple C-shaped clips 1208 to one another and the bracket 1210 may couple the C-shaped clips 1208 to the indicator receiving portion 1216 of the example smart cap.

Thus, provided is an example wine inventory management system designed to assist a user in efficiently selecting and locating a wine from a collection. In one example, the wine inventory management system may comprise a smart cap having an indicator portion and a processor communicatively coupled with the smart cap. The processor communicatively coupled with the smart cap may include a determining module that determines a first set of criteria, a matching module that matches wines to the first set of criteria to form a first wine set, and an illuminating module that illuminates smart caps for the first wine set, in some examples. In one embodiment, the first set of criteria may be based on user wine preferences. The user wine preference may be based on a user wine search via a wine inventory application, for example.

In one embodiment, the determining module may determine a second set of criteria, and the matching module may match wines to the second set of criteria to form a second wine set. The second set of criteria may also be based on a user wine search. In some examples, the second set of criteria may be based on selection of a category, application of a filter to wine search results, or selection of a wine.

A cap (i.e., smart cap) of an example wine inventory management system may include an indicator portion, a mounting portion attached to the indicator portion, one or more indicator lights viewable from an exterior of the indicator portion, and a microcontroller positioned within the indicator portion. In some examples the microcontroller may be executable for illuminating the indicator lights responsive to a request. The cap may further include a button positioned in the indicator portion, and the microcontroller may be executable to illuminate indicator lights responsive to the button receiving a user input.

An example method for a wine inventory management system may include receiving a first set of criteria, determining that one or more wines of a wine collection satisfies the first set of criteria to form a first wine set, and illuminating smart caps for the first wine set. In some examples, the method may further include receiving a second set of criteria and determining that one or more wines of a wine collection satisfies the second set of criteria to form a second wine set. The second set of criteria may be based on a condition of the wines in some examples. In some embodiments, smart caps for the second wine set may also be illuminated. For example, the smart caps for the second wine set may be dimmed compared to the smart caps illuminated for the first wine set. The criteria for the first set and the second set may be received responsive to a user wine search via a wine inventory application. In some examples, more than two sets of criteria may be possible.

It will be appreciated that the configurations and/or approaches described herein are exemplary in nature, and that these specific embodiments or examples are not to be considered in a limiting sense, because numerous variations are possible. The subject matter of the present disclosure includes all novel and nonobvious combinations and subcombinations of the various features, functions, acts, and/or properties disclosed herein, as well as any and all equivalents thereof.

The invention claimed is:

1. A wine inventory management system, comprising:
a plurality of smart caps that are each coupled to a wine of a wine collection, respectively, and wherein each of the smart caps has an indicator portion; and
a processor communicatively coupled with the plurality of smart caps, comprising:
a determining module that determines a first set of criteria, wherein the first set of criteria includes a wine type and a wine drinkability, wherein the wine drinkability is a current wine condition relative to a peak wine condition;
a matching module that matches one or more wines of the wine collection to the first set of criteria to form a first wine set, the matching based on the wine type and based on a calculation of the wine drinkability for each of the one or more wines, wherein the wine drinkability for each of the one or more wines is calculated based on an amount of time that has passed since the one or more wines were bottled and one or more environmental sensor outputs;
an illuminating module that illuminates smart caps for the first wine set; and
a wine database update receiving module that automatically updates a database to remove one wine of the wine collection from an inventory, the database updated responsive to a smart cap of the plurality of smart caps being removed from the one wine.

2. The wine inventory management system of claim 1, wherein the determining module determines a second set of criteria and the matching module matches wines to the second set of criteria to form a second wine set.

3. The wine inventory management system of claim 2, wherein the illuminating module illuminates the smart caps for the first wine set and smart caps for the second wine set.

4. The wine inventory management system of claim 1, wherein the wine drinkability is calculated via a wine aging algorithm.

5. The wine inventory management system as in any of claim 3, wherein the smart caps for the second wine set are dimmed compared to the smart caps for the first wine set.

6. The wine inventory management system of claim 5, wherein the second set of criteria includes a current condition of a wine.

7. The wine inventory management system of claim 1, wherein illuminating the plurality of smart caps includes illuminating the plurality of smart caps with light animation patterns.

8. A method for a wine inventory management system, comprising:
receiving a first set of criteria, wherein the first set of criteria includes a request to indicate a wine condition relative to a peak condition for each wine of a wine collection that includes a plurality of wines, and wherein each of the plurality of wines of the wine collection includes a smart cap positioned thereon;
calculating the wine condition relative to the peak condition for each of the plurality of wines of the wine collection to form a plurality of wine sets, wherein each of the plurality of wine sets is a different condition relative to the peak condition, and wherein the wine condition relative to the peak condition is calculated based on an amount of time that has passed since the wine was bottled and one or more environmental sensor outputs;
illuminating smart caps for each of the plurality of the wine sets a different color; and
automatically updating a database to remove one of the plurality of wines from an inventory of the wine collection responsive to the smart cap corresponding to the one of the plurality of wines being removed.

9. The method of claim 8, further comprising receiving a second set of criteria.

10. The method as in claim 9, further comprising determining that one or more wines of the wine collection satisfies the second set of criteria to form a second wine set.

11. The method of claim 10, further comprising illuminating smart caps for the second wine set.

12. The method of claim 11, wherein the smart caps for the second wine set are dimmed compared to the smart caps for the first wine set.

13. The method of claim 8, wherein the wine condition is calculated via a wine aging algorithm.

14. A cap, comprising:
an indicator portion;
a mounting portion attached to the indicator portion;
one or more indicator lights viewable from an exterior of the indicator portion; and
a microcontroller positioned within the indicator portion, wherein the microcontroller is executable for illuminating the indicator lights responsive to a request received from a processor communicatively coupled to the cap,
wherein the processor sends the request to the cap responsive to determining that a wine associated with the cap matches a first set of criteria,
wherein the first set of criteria includes a type of wine and a wine drinkability, wherein the wine drinkability is a current wine condition relative to a peak wine condition, the wine drinkability calculated based on one or more environmental sensor outputs of the cap, an amount of time that has passed since the wine was bottled, and an alcohol content of the wine.

15. The cap of claim 14, wherein the environmental sensor outputs include temperature and barometric pressure outputs.

16. The cap of claim 14, wherein the cap is communicatively coupled to a wine inventory application of a wine inventory management system via a wireless communication link.

17. The cap of claim 14, wherein the illuminating includes illuminating the indicator lights in different colors based on the request.

18. The cap of claim 14, wherein the wine drinkability is further calculated based on a pH of the wine and a residual sugar of the wine.

19. The cap of claim 15, wherein the wine drinkability is further calculated based on a tannin content of the wine.

20. The cap of claim 14, wherein the mounting portion comprises one or more projections that are biased in an inward direction.

* * * * *